United States Patent
Ke et al.

(10) Patent No.: US 9,057,728 B2
(45) Date of Patent: Jun. 16, 2015

(54) FACS-BASED METHOD FOR OBTAINING AN ANTIBODY SEQUENCE

(75) Inventors: Yaohuang Ke, San Francisco, CA (US); Guo-Liang Yu, Hillsborough, CA (US); Karin Vroom, South San Francisco, CA (US)

(73) Assignee: Epitomics, Inc., Burlingame, CA (US)

( * ) Notice: Subject to any disclaimer, the term of this patent is extended or adjusted under 35 U.S.C. 154(b) by 244 days.

(21) Appl. No.: 13/545,857

(22) Filed: Jul. 10, 2012

(65) Prior Publication Data
US 2013/0017555 A1 Jan. 17, 2013

Related U.S. Application Data

(60) Provisional application No. 61/506,953, filed on Jul. 12, 2011.

(51) Int. Cl.
*G01N 33/564* (2006.01)
*G01N 33/569* (2006.01)
*G01N 33/68* (2006.01)
*G01N 33/50* (2006.01)

(52) U.S. Cl.
CPC ...... *G01N 33/56972* (2013.01); *G01N 33/6854* (2013.01); *G01N 33/564* (2013.01); *G01N 33/5032* (2013.01); *G01N 33/5047* (2013.01)

(58) Field of Classification Search
None
See application file for complete search history.

(56) References Cited

U.S. PATENT DOCUMENTS

| 4,510,244 A | 4/1985 | Parks et al. |
|---|---|---|
| 4,859,595 A | 8/1989 | Strosberg et al. |
| 4,977,081 A | 12/1990 | Raybould et al. |
| 5,472,868 A | 12/1995 | McCormack et al. |
| 5,610,034 A | 3/1997 | Nyyssonen et al. |
| 6,372,214 B1 | 4/2002 | Prusiner et al. |
| 2001/0036647 A1 | 11/2001 | Choudary et al. |
| 2004/0067496 A1* | 4/2004 | Pytela et al. ............... 435/6 |
| 2006/0211088 A1* | 9/2006 | Hermans et al. ........... 435/69.1 |
| 2008/0241822 A1* | 10/2008 | Wyrick et al. ............... 435/6 |

FOREIGN PATENT DOCUMENTS

WO WO2007003041 1/2007

OTHER PUBLICATIONS

Babcook, et al., "A novel strategy for generating monoclonal antibodies from single, isolated lymphocytes producing antibodies of defined specificities", Proc Natl Acad Sci, Jul. 1996, 93(15):7843-8.

(Continued)

*Primary Examiner* — Gail R Gabel
(74) *Attorney, Agent, or Firm* — James S. Keddie; Bozicevic, Field & Francis, LLP

(57) ABSTRACT

In certain embodiments, the method may comprises: a) contacting a population of permeabilized, cross-linked antibody-producing cells with a labeled antigen to produce a labeled sample in which cells that produce an antibody that specifically binds to said antigen are intracellularly labeled; b) using FACS to isolate cells that are intracellularly labeled, thereby producing labeled cells; c) uncrosslinking said labeled cells to produce uncrosslinked cells; and d) amplifying heavy and light chain-encoding nucleic acid from individual uncrosslinked cells, thereby obtaining nucleic acid that encodes the variable domain of antibody that specifically binds to said antigen.

16 Claims, 15 Drawing Sheets

(56) References Cited

OTHER PUBLICATIONS

Becker, et al., "Somatic diversification of immunoglobulin heavy chain VDJ genes: evidence for somatic gene conversion in rabbits", Cell, Nov. 1990, 63(5):987-97.
Bos, et al., "Humoral immune response to 2,4-dinitrophenyl—keyhole limpet hemocyanin in antigen-free, germ-free and conventional BALB/c mice", Eur J Immunol, Jan. 1994, 24(1):59-65.
Calame, "Plasma cells: finding new light at the end of B cell development", Nat Immunol, Dec. 2001, 2 (12):1103-8.
Coronella, et al., "Amplification of IgG VH and VL (Fab) from single human plasma cells and B cells", Nucleic Acids Res, Oct. 2000, 28(20):E85.
De Wildt, et al., "A new method for the analysis and production of monoclonal antibody fragments originating from single human B cells", J Immunol Methods, Aug. 1997, 207(1):61-7.
Durocher, et al., "High-level and high-throughput recombinant protein production by transient transfection of suspension-growing human 293-EBNA1 cells", Nucleic Acids Res, Jan. 2002, 30(2):E9.
Friedmann, et al. "Neonatal VH, D, and JH gene usage in rabbit B lineage cells", J Immunol, Jan. 1994, 152 (2):632-641.
Huse, et al., "Generation of a large combinatorial library of the immunoglobulin repertoire in phage lambda. 1989.", Biotechnology, 1992, 24:517-23.
Jiang, et al., "A novel strategy for generation of monoclonal antibodies from single B cells using rt-PCR technique and in vitro expression", Biotechnol Prog, Jul.-Aug. 2006, 22(4):979-88.
Knight, et al., "Molecular basis of the allelic inheritance of rabbit immunoglobulin VH allotypes: implications for the generation of antibody diversity", Cell, Mar. 1990, 60(6):963-70.
Lightwood, et al., "Antibody generation through B cell panning on antigen followed by in situ culture and direct RT-PCR on cells harvested en masse from antigen-positive wells", J Immunol Methods, Oct. 2006, 316(1-2):133-43.
Marks, et al., "By-passing immunization. Human antibodies from V-gene libraries displayed on phage", J Mol Biol, Dec. 1991, 222(3):581-97.
Ochsenbein, et al., "Protective long-term antibody memory by antigen-driven and T help-dependent differentiation of long-lived memory B cells to short-lived plasma cells independent of secondary lymphoid organs", Proc Natl Acad Sci, Nov. 2000, 97(24):13263-8.
Orlandi, et al., "Cloning immunoglobulin variable domains for expression by the polymerase chain reaction", Proc Natl Acad Sci, May 1989, 86(10):3833-7.
Sabrina, et al., "In vitro generation of anti-hepatitis B monoclonal antibodies from a single plasma cell using single-cell RT-PCR and cell-free protein synthesis", J Biosci Bioeng, Jan. 2010, 109(1):75-82.
Sastry, et al., "Cloning of the immunological repertoire in *Escherichia coli* for generation of monoclonal catalytic antibodies: construction of a heavy chain variable region-specific cDNA library", Proc Natl Acad Sci, Aug. 1989, 86 (15):5728-32.
Sehgal, et al., "Analyses of single B cells by polymerase chain reaction reveal rearranged VH with germline sequences in spleens of immunized adult rabbits: implications for B cell repertoire maintenance and renewal", J Immunol, Nov. 1998, 161(10):5347-56.
Slifka, et al., "Long-lived plasma cells: a mechanism for maintaining persistent antibody production", Curr Opin Immunol, Jun. 1998, 10(3):252-8.
Spieker-Polet, et al., "Rabbit monoclonal antibodies: generating a fusion partner to produce rabbit-rabbit hybridomas", Proc Natl Acad Sci, Sep. 1995, 92(20):9348-52.
Takahashi, et al., "The direct cloning of the immunoglobulin VH genes from primary cultured B cells specific for a short peptide", J Biotechnol, Aug. 1996, 49(1-3):201-10.
Tiller, et al., "Cloning and expression of murine Ig genes from single B cells", J Immunol Methods, Oct. 2009, 350(1-2):183-93.
Tiller, et al., "Efficient generation of monoclonal antibodies from single human B cells by single cell RT-PCR and expression vector cloning", J Immunol Methods, Jan. 2008, 329(1-2):112-24.
PCT/US12/46098, PCT Notification of Transmittal of the International Search Report and the Written Opinion of the International Searching Authority, or the Declaration, Sep. 2012, 12 pages.
Krutzik, et al. "Intracellular phospho-protein staining techniques for flow cytometry: monitoring single cell signaling events", Cytometry A. Oct. 2003;55(2):61-70.
Communication, The Extended European Search Report mailed on Apr. 8, 2015 for European patent application serial No. 12810553.3, 7 pages.

* cited by examiner

Antibody producing cells

↓ crosslink, permeabilize and label using labeled antigen

↓ FACS sort the labeled cells

↓ uncrosslink

↓ PCR antibody sequences light chain   heavy chain

↓ sequence

Heavy chain sequence
Light chain sequence

Sequences of the heavy chain variable region with signal peptides

```
                       Signal Peptide
gi|E8H-1    --GCTTCTCCTGGTCGCTGTGCTGTGTCAAAGGTGTCCAGTGTCAG------TCGGTTGGAGGAGAGTCCG
gi|C6H-1    -GCTTCTCCTGGTCGCTGTGCTGTGTCAAAGGTGTCCAGTGTCAG------TCGGAGGAGGAGAGTCCG
gi|F3H-2    AGCTTCTCCTGGTCGCTGTGCTGTGTCAAAGGTGTCCAGTGTCAG------TCGGTTGGAGGAGAGTCCG
gi|E9H-2    -GCTTCTCCTGGTCGCTGTGTTGCTGTCAAAGGTGTCCAGTGTCAG------TCGGTTGGAGGAGAGTCCG
gi|C9H-1    --GCTTCTCCTGGTCGCTGTGCTGTGTCAAAGGTGTCCAGTGTCAG------TCGGTGGAGGAGAGTCCG
gi|D10H-1   ---GCTTCTCCTGGTCGCTGCTGTGTCCAGTGTCAAAGGTGTCCAGTGTCAG------TCGCTGGAGGAGAGTCCG
gi|C8H-1    ---GCTTCTCCTGGTCGCTGCTGTGTGCTGTCCCAGTGTCAAAGGTGTCCAGTGTCAG------TCGGTGGAGGAGAGTCCG
gi|C11H-1   ---GCTTCTCCTGGTCGCTGCTGTGTGCCCAGTGTCAAAGGTGTCCAGTGTCAG------TCGCTGGAGGAGAGTCCG
gi|D3H-1    --GCTTCTCCTGGTCGCTGCTGTGTGCTGTCCCAGTGTCAAAGGTGTCCAGTGTCAG------TCGTTGGAGGAGAGTCCG
gi|C3H-1    -GCTTCTCCTGTCGCTGCTGTGTGCTGTCCCAGTGTCAAAGGTGTCCAGTGTCAG------TCGTTGGAGGAGAGTCCG
gi|E3H-1    -GCTTCTCCTGGTCGCTGCTGTGTGCTGTCCCAGTGTCAAAGGTGTCCAGTGTCAG------TCGTTGGAGGGGTCCG
             **  *******  * *       ****           *      * ***  ** gi|E8H-1    GGGGTCGCCCTGGTCTCGCTCAGCCTGGGACACCCCTGACACTCACCTGCACAGTCTCTGGAATCG
gi|C6H-1    GGGGTCGCCCTGGTCACGCTCAGCCTGGGACACCCCTGACACTCACCTGCACACGGTCTCTGGATTCT
gi|F3H-2    GGGGTCGCCCTGGTCACGCTCAGCCTGGGACACCCCTGACACTCACCTGCACCGTCTCTGGATTCT
gi|E9H-2    GGGGTCGCCCTGGTCACGCTCAGCCTGGGACACCCCTGACACAGTCACCTGCACAGTCTCTGGAATCG
gi|C9H-1    GGGGTCGCCCTGGTCGGTAACGCCTGGGAGGGTCCCTGACACTCACCTGCACAGTCTCTGGAATCG
gi|D10H-1   GGGGAGGTCGCTGGTCCAGGCTGACCTGAGGGATCCCTGACACTCACCTGCACACAGTTCTGGATTCT
gi|C8H-1    GGGGAGGCCTGGTCCAGGCTGAGGGATCCCTGAGGGCATCCCTGACACTCACCTGCCAAGTCTCTGGATTCT
gi|C11H-1   GGGGAGCCCTGGTCAAGCCTCAGCCTGGGCTGAGGGCATCCCTGACACTCACCTGTACAGCCTCTGGATTCT
gi|D3H-1    GGGGAGACCTGGTCAAGCCTCAGCCTGGGGCCTCCCTGACACTCACCTGCACAGCCTCTGGATTCT
gi|C3H-1    GGGGAGACCTGGTCAAGCCTCAGCCTGGGGCCTCCCTGACACTCACCTGCACAGCCTCTGGATTCT
gi|E3H-1    GGGGAGACCTGGTCAAGCCTCAGCCTGGGGCCTCCCTGACACTCACCTGCCAAAGTCTCTGGATTCT
            ****     *******   *  *          * **     ** *** ** *******  ******
```

FIG. 8A

CDR1

| | |
|---|---|
| gi\|E8H-1 | ACCTCAGC------AACTACGACATGAACTGGGTCCGCCAGGCTCCAGGGGAGGGGCTGGAAT |
| gi\|C6H-1 | CCCTCAGT------AGGTACTGGATAGCCTGGGTCCGCCAGGCTCCAGGGAAGGGGCTGGAAT |
| gi\|F3H-2 | CCCTCAGT------GCCAATGCAATAACCTGGGTCCGTCAGGCTCCAGGGAAGGGGCTGGAAT |
| gi\|E9H-2 | ACCTCAGT------AGCTCTGCAATGAGCTGGGTCCGCCAGGCTCCAGGGAAGGGGCTGGAAT |
| gi\|C9H-1 | ACCTCAGT------ACCTATGAAATAAGCTGGGTCCGCCAGGCTCCAGGGAAGGGGCTGGAAT |
| gi\|D10H-1 | ACCTCAGT------ACTTATGCAATGGCAATGGGATATGCTGGGCTCCAGGCTCCAGGGAAGGGGCTGGAGT |
| gi\|C8H-1 | CCTTCAATGGCAACTACTACTGGATATGCTGGGCTCCAGGCTCCAGGGAAGGGGCTGGAGT |
| gi\|C11H-1 | ACTTCAGTTACTACTACTAGCTACATGTGCTGGGTCCGCCAGGCTCCAGGGAAGGGGCTGAGT |
| gi\|D3H-1 | CCCTCAGTAGTACTAGCTACTACTACATGTGCTGGGTCCGCCAGGCTCCAGGGAAGGGCCTGAGT |
| gi\|C3H-1 | CCCTCAGTAACGGCTACTACATGTGCTGGGTCCGCCAGGCTCCAGGGAAGGGGCTGGAAT |
| gi\|E3H-1 | CCTTCAGTAGCGGGCTACTACTACATGTGCTGGGTCCGCCAGGCTCCAGGGAAGGGGCTGGAGT |
| | * ** ** ****** * |

CDR2

| | |
|---|---|
| gi\|E8H-1 | GGATCGGTGTCATG--------TATAATTATGGCAGCGCATACTACTACGCGAACTGGGCGAAAG |
| gi\|C6H-1 | ATATCGGAATCATT--------AGTAGTACTGGTAGTACCACATACTACGCGAACTGGGCGAAAG |
| gi\|F3H-2 | GGATCGGAATCATT--------CTTACTCTTGATACCACATACTACGCGACCTGGGCGAAGG |
| gi\|E9H-2 | GGATCGGAATCATT--------GGCAATAATGGTGGCACACATACTACGCGACTTGGGCGAAAG |
| gi\|C9H-1 | GGATCGGAATCATT--------GGTACTAGCGCTAACACAGTCTACGCGAGCTGGGCGAAAG |
| gi\|D10H-1 | GGATCGGCATGCATTTATGGTGGTACTAGTGGTAGCACTACGCGCGAGCTGGGCGAAAG |
| gi\|C8H-1 | TGATCACATGCATT-----GGTACTAGTCGTAGTAGTGTACTACCACATGGTACGCGAGCTGGGTGAAAG |
| gi\|C11H-1 | GGATCGGGTG----TTTTACTACTGGTAGTGGTAGTGATACTGACTACGCGAACTGGGCGAACA |
| gi\|D3H-1 | GGATCGGATG----TTTTACTACTGGCAGTGACAGACCACTACGCGAACTGGGCGAACA |
| gi\|C3H-1 | GGATCGGCATGCATTTATGCTGGTGATAGTGGTCGCAGTACTTACTACGCGCGCTGGGCGAAAG |
| gi\|E3H-1 | GGATCGGCATGCATTTATGCTGGTAGTAGTGGTAGTACTTACTACGCGAACTGGGCGAAAG |
| | *** * *** ****** * |

```
gi|E8H-1    GTGATCCTGGG----GACATCTGGGGCCCAGGCACCCTGGTCACCGTCTCCTTA
gi|C6H-1    ATGAGCGTGGGTTTGATATATGGGGCCCAGGCACCCTGGTCACCGTCTCCTTA
gi|F3H-2    GTTTTTGGGCCTTTGACATCTGGGGCCCAGGCACCCTGGTCACCGTCTCCTTG
gi|E9H-2    ATAATTACACCATGCACCCCTGGGGCCCAGGACCCTGGTCACCGTCTCTTCA
gi|C9H-1    GTATTCATGCTTTTCATCCCTGGGGCCCAGGCACCCTGGTCACCGTCTCCTCA
gi|D10H-1   GTTTTGGTGCTTTTGATCCCTGGGGCCCAGGCACCCTGGTCACCGTCTCCTCA
gi|C8H-1    ATAATCATGCGCTTGCTATCTGGGGCCCAGGCACCCTGGTCACCGTCTCCTTA
gi|C11H-1   GTTTCTATGCCATGGACTTCTAGGGCCCAGGGACCCTCGTCACCGTCTCTTCA
gi|D3H-1    GTTTCTACGCCATGGACCCTCGTGTGGGGCCCAGGCACCCTGGTCACCGTCTCCTCA
gi|C3H-1    CTTATACATACTTCACCTTGTGGGGCCCAGGCACCCTGGTCACCGTCTCCTCA
gi|E3H-1    CTTATACATACTTCACCTTTTGGGCCCAGGCACCCTGGTCACCGTCTCCTCA
            *              *  ********  ***** ********** *******  *
```

FIG. 8D

Sequences of the light chain variable region with signal peptides

```
                      Signal Peptide
gi|C11L-1    GCTGCTGGGGCTCCTCCTGCTCTGGCTCTCCCAGGTGCCAGATGT----GC----ATTCGAATT
gi|D3L-1     GCTGCTGGGGCTCCTCCTGCTCTGGCTCTCCCAGGTGCCAGATGT----GC----ATTCGAGTT
gi|C3L-1     GCTGCTGGGGCTCCTCCTGCTCTGGCTCTCCCAGGTGCCAGATGT----GCCGAAGTAGTGAT
gi|E3L-2     GCTGCTGGGGCTCCTCCTGCTCTGGCTCTCCCAGGTGCCAGATGT-----GCCGAAGTAGTGAT
gi|F3L-1     GCTGCTGGGTCTCCTGCTCTGGCTCTCCCAGGTGCCAGATGT-----GCCGAAGTAGTGAT
gi|C8L-1     GCTGCTGGGGCTCCTCCTGCTCTGGCTCTCCCAGGTGCCAGATGT----G----ATGTTGTGAT
gi|E9L-1     GCTGCTGGGGCTCCTCCTGCTCTGGCTCTCCCAGGTGCCAGATGT---G---ATGTTGTGAT
gi|C9L-1     GCTGCTGGGGCTCCTCCTGCTCTGGCTCTCCCAGGTGCCAGATGT----GCC-----GTCGTGCT
gi|C6L-1     GCTGCTGGGGCTCCTCCTGCTCTGGCTCTCCCAGGTGCCACATTTGCT-------CAAGTGGT
gi|D10L-1    GCTGCTGGGGCTCCTCCTGCTCTGGCTCTCCCAGGTGCCAGATGT---GCC---GTCGTGAT
gi|E8L-1     GCTGCTGGGGCTCCTCCTGCTCTGGCTCTCCCAGGTGCCACATTTGCC---------ATCGTGAT
             ***********  **********************  *       *   * gi|C11L-1    GACCCAGACTCCATCCTCCGTGTCTGCAGCTGTGGGAGACACAGTCACCATCAAGTGCCA
gi|D3L-1     GACCCAGACTCCATCCTCCGTGTGGAGGCAGCTGTGGGAGGCACAGTCACCATCAAGTGCCA
gi|C3L-1     GACCCAGACTCCAGCTCCGTGTGGAGGCAGCTGTGGGAGGCACAGTCACCATCAAGTGCCA
gi|E3L-2     GACCCAGACTCCAGCTCCGTGTGGAGGCAGCTGTGGGAGGCACAGTCACCATCAAGTGCCA
gi|F3L-1     GACCCAGACTCCAGCTCCAGCCTCCGTGTGGAGGCAGCTGTGGGAGGCACAGTCACCATCAAGTGCCA
gi|C8L-1     GACCCAGACTCCAGCTCCAGCCTCCGTGTGGAGGCAGTTGTGGGAGGCACAGTCACCATCAAGTGCCA
gi|E9L-1     GACCCAGACTCCAGCTCCAGCCTCCGTGTGGAGGCGGGCTGTGGGAGGCACAGTCACCATCAAGTGCCA
gi|C9L-1     GACCCAGACTCCAGCTCCAGCCTCGTGTCTGAACCTGGGAGGCACAGTCACCATCAATTGCCA
gi|C6L-1     GACCCAGACTCCATCCCCCGTGTCTGCACCTGTGCAGCTGTGGGAGGCACAGTCACCATCAATTGCCA
gi|D10L-1    GACCCAGGCTGAATCGCCCCGTGTCTGCACCTGTGCAGCTGTGGGAGGCACAGTCACCATCAATTGCCA
gi|E8L-1     GACCCAGACTCCATCTTCCAAGTCTGTCCCGTGGGAGACACAGTCACCATCAATTGCCA
             *********   **   **    *    *  *  *  ***************  *****
```

FIG. 9A

CDR1

```
gi|C11L-1   GGCCAGTCAGAGAGCATTAGTAGCTAC----------TTAGCCTGGTATCAGCAGAAACCAGGGCA
gi|D3L-1    GGCCAGTGAGAGAGCATTGGTAGCTAC----------TTAGCCTGGTATCAGCAGAAACCAGGGCA
gi|C3L-1    GGCCAGTCAGAGAGGTTTGACACCAAT----------TTAGCCTGGTATCAGCAGAAACCAGGGCA
gi|E3L-2    GGCCAGTCAGAGTATTGATAGTAAT------------TTAGCCTGGTATCAGCAGAAACCAGGGCA
gi|F3L-1    GGCCAGTCAGAGCATTGGTAGTGCC------------TTATCCTGGTATCAGCAGAAACCTGGGCA
gi|C8L-1    GGCCAGTGAAGATATTAATAGATAC------------TTAGCCTGGTATCAGCAGAAACCAGGGCA
gi|E9L-1    GGCCAGTCAGAGAATATCTACAGGTCT----------TTAGCCTGGCATCAGCAGAAACCAGGGCA
gi|C9L-1    GGCCAGTCAGAGCATTAGCAATGCA------------TTAGCCTGGTATCAGCAGAAACCAGGGCA
gi|C6L-1    GGCCAGTCAGAGTCTTGATGATGACAACTGGTTATCTGGTATCAGCAGAAACCAGGGCA
gi|D10L-1   GGCCAGTCAGAGTATTAGTAGTAGCTAC---------TTATCCTGGTATCAGCAGAAACCAGGGCA
gi|E8L-1    GGCCACTGAGAGTGTTTATAGTAACAACCGCTTAGCCTGGTATTAGCAGAAACCAGGTCA
                *****  *      *                      ** *****  ** ************ **
```

CDR2

```
gi|C11L-1   GCCTCCCAAGCTCCTGATCTACAAGGCATCCACTCTGGGGTCCCATCGCGGTT
gi|D3L-1    GCCTCCCAAGCTCCTGATCTACATGGCATCCAGCCATCTGGGTCCCATCACGGTT
gi|C3L-1    GCCTCCCAAGCTCCTGATCTATTCTGCATCTGCATCCACTGGGTCCCATCGCGGTT
gi|E3L-2    GCCTCCCAAGCTCCTGATCTATGGTGCATCTATGGTACATCCACTCTGGCATCTGGCATCCCATCGCGGTT
gi|F3L-1    GCCTCCCAAGCTCCTGATCTATGGTGCATCTATGGTACATCCACTCTGGCATCTGGCATCCCATCGCGGTT
gi|C8L-1    GCCTCCCAAGCTCCTGATCTACAGGGCATCTATGGTGCATCCACTCTGGCATCTGGCATCCCATCGCGGTT
gi|E9L-1    GCCTCCCAAGCTCCTGATCTATGCTGCATCCACTCTGGCATCTGGCATCCCATCGCGGTT
gi|C9L-1    GCCTCCCAAGCTCCTGATCTATGCTGCATCCACTCTGGCATCTGGAATCTGGCATCCCATCGCGGTT
gi|C6L-1    GCCTCCCAAGCTCCTGATCTACTTTTTGCATCCACTCTACTCCACTCTGGCATCTGGCATCCCATCGCGGTT
gi|D10L-1   GCCTCCCAAGCTCCTGATCTACGAAGCATCCAAACTGGCATCTGGCATCTGGCATCCCATCGCGGTT
gi|E8L-1    GCCTCCCAAGCTCCTGATCTATCTGGCATCTGGCATCCACTCTGGCATCTGGCATCCCATCGCGGTT
                ***************  *   *  *  *   * *  ***************
```

```
gi|C11L-1   ..........
gi|D3L-1    TGCTTTTCGGCGGAGGGACCGAGGTGGTCGTCGTCAAA
gi|C3L-1    TGCTTTTCGGCGGAGGGACTGAGGTGGTCGTCGTCAAA
gi|E3L-1    TGCTTTTCGGCGGAGGGACCGAGGTGGTCGTCGTCAAA
gi|F3L-2    TTCTTTTCGGCGGAGGGACCGAGGTGGTCGTCGTCAAA
gi|C8L-1    TGGTTTTCGGCGGAGGGACCGAGGTGGTCGTCGTCAAA
gi|E9L-1    TGCTTTTCGGCGGAGGGACCGAGGTGGTCGTCGTCAAA
gi|C9L-1    TGCTTTTCGGCGGAGGGACCGAGGTGGTCGTCGTCAAA
gi|C6L-1    TGCTTTTCGGCGGAGGGACCGAGGTGGTCGTCGTCAAA
gi|D10L-1   TGGTTTTCGGCGGAGGGACCGAGGTGGTGGTCGTCAAA
gi|E8L-1    TGCTTTTCGGCGGAGGGACCGAGGTGGTGGTCGTCAAG
            *  ****** *** ***** ******** **** ****
```

FIG. 9D

```
                        SEQUENCE LISTING

<160> NUMBER OF SEQ ID NOS: 22

<210> SEQ ID NO 1
<211> LENGTH: 448
<212> TYPE: DNA
<213> ORGANISM: Oryctolagus cuniculus

<400> SEQUENCE: 1
gcttctcctg gtcgctgtgc tcaaaggtgt ccagtgtcag tcggtggagg agcccggggg      60
tcgcctggtc tcgcctggga cacccctgac actcacctgc acagtctctg gaatcgacct    120
cagcaactac gacatgaact gggtccgcca ggctccaggg gaggggctgg aatggatcgg    180
tgtcatgtat aattatggca gcgcatacta cgcgaactgg gcgaaaggcc gattcaccat    240
ctccaaaacc tcgaccacgg tggagctgaa aatcatcagt ccgacaattg aggacacggc    300
cacttatttc tgtgtcagag ggagtggtag tgatcctggg gacatctggg gcccaggcac    360
cctggtcacc gtctccttag ggcaacctaa ggctccatca gtcttcccac tggccccctg    420
ctgcggggac gcacccagct ccacggtg                                       448

<210> SEQ ID NO 2
<211> LENGTH: 460
<212> TYPE: DNA
<213> ORGANISM: Oryctolagus cuniculus

<400> SEQUENCE: 2
gcttctcctg gtcgctgtgc tcaaaggtgt ccagtgtcag tcggaggagg agtccggggg      60
tcgcctggtc acgcctggga cacccctgac actcacctgc acggtctctg gattctccct    120
cagtaggtac tggatagcct gggtccgcca ggctccaggg gaggggctgg aatatatcgg    180
aatcattagt agtactggta ggacatacta cgcgaactgg gcgaaaggcc gattcaccat    240
ctccaagtcc tcgccgacca cggtggattt gaaattgacc agtctgacaa ccgaggacac    300
gaccacctat ttctgtgcca gaggaagaga tgctatttat gagcgtgggt ttgatatatg    360
gggcccaggc accctggtca ccgtctcctt agggcaacct aaggctccat cagtcttccc    420
actggccccc tgctgcgggg acacacccag ctccacggtg                          460

<210> SEQ ID NO 3
<211> LENGTH: 458
<212> TYPE: DNA
<213> ORGANISM: Oryctolagus cuniculus
```

<400> SEQUENCE: 3

```
agcttctcct ggtcgctgtg ctcaaaggtg tccagtgtca gtcggtggag gagtccgggg      60
gtcgcctggt cacgcctggg acacccctga cagtcacctg caccgtctct ggattctccc     120
tcagtgccaa tgcaataacc tgggtccgtc aggctccagg gaaggggctg aatggatcg      180
gaatcattct tactcttgat accacatact acgcgacctg ggcgaagggc cgattcacca     240
tctccagaac ctcgtcgacc acggtggatc tgaaaatcac cagtccgaca accgaggaca     300
cggccaccta tttctgcgcc agagatgatg tgttggtttt tgggcctttt gacatctggg     360
gcccaggcac cctggtcacc gtctccttgg ggcaacctaa ggctccatca gtcttcccac     420
tggcccctg ctgcggggac acccagct ccacggtg                                458
```

<210> SEQ ID NO 4
<211> LENGTH: 457
<212> TYPE: DNA
<213> ORGANISM: Oryctolagus cuniculus

<400> SEQUENCE: 4

```
gcttctcctg gtcgctgtgt tcaaaggtgt ccagtgtcag tcggtggagg agtccggggg      60
tcgcctggtc acgcctggga caccctgac actcacctgc acagtctctg gaatcgacct     120
cagtagctct gcaatgagct gggtccgcca ggctccaggg aaggggctgg aatggatcgg     180
aatcattggc aataatggtg gcacatacta cgcgacttgg gcgaaggcc gattcaccat      240
ctccaaaacc tcgaccacgg tggatctgaa aatgaccagt ccgacaaccg aggacacggc     300
cacctatttc tgtgccagag gtgctggtag taagaataat tacaccatgc accctgggg    360
cccagggacc ctcgtcaccg tctcttcagg gcaacctaag gctccatcag tcttcccact     420
ggccccctgc tgcggggaca cccagctc cacggtg                                457
```

<210> SEQ ID NO 5
<211> LENGTH: 457
<212> TYPE: DNA
<213> ORGANISM: Oryctolagus cuniculus

<400> SEQUENCE: 5

```
gcttctcctg gtcgctgtgc tcaaaggtgt ccagtgtcag tcgctggagg agtccggggg      60
tcgcctggta acgcctggag ggtccctgac actcacctgc acagtctctg gaatcgacct     120
cagtacctat gaaataagct gggtccgcca ggctccaggg aaggggctgg aatggatcgg     180
aatcattggt actagcgcta acacagtcta cgcgagctgg gcgaaggcc gattcaccat      240
ctccaaatcc tcgaccacgg tggatctgag ggtgaccagt ctgacaaccg aggacacggc     300
cacctatttc tgtgcccgtg cctacgatga atatggtatt catgctttc atccctgggg     360
cccaggcacc ctggtcaccg tctcctcagg gcaacctaag gctccatcag tcttcccact     420
ggccccctgc tgcggggaca cccagctc cacggtg                                457
```

<210> SEQ ID NO 6
<211> LENGTH: 472
<212> TYPE: DNA
<213> ORGANISM: Oryctolagus cuniculus

<400> SEQUENCE: 6

```
gcttctcctg gtcgctgtgc tcaaaggtgt ccagtgtcag tcgctggagg agtccggggg      60
tcgcctggtc acgcctggag gatccctgac actcacctgc acagtctctg gaatcgacct     120
cagtacttat gcaatgggct gggtccgcca ggctccaggg aaggggctgg agtggatcgc     180
```

```
atgcatttat ggtggtagta gtggtagcac tcactacgcg cgctgggcga aaggccgagt    240
caccatctcc aaaacctcga ccacggtgga tctgaaaatc accagtccga cagccgagga    300
cacggccacc tatttctgtg ccagagatat ttattcttat agttactggg gttttggtgc    360
ttttgatccc tggggcccag gcaccctggt caccgtctcc tcagggcaac ctaaggctcc    420
atcagtcttc ccactggccc ctgctgcgg ggacacaccc agctccacgg tg             472

<210> SEQ ID NO 7
<211> LENGTH: 463
<212> TYPE: DNA
<213> ORGANISM: Oryctolagus cuniculus

<400> SEQUENCE: 7
gcttctcctg gtcgctgtgc tcaaaggtgc ccagtgtcag gagcagctgg tggagtccgg     60
gggagggctg gtccaggctg agggatccct gacactcacc tgcacagctt ctggattctc    120
cttcaatggc aactactgga tatgctgggc ccgccaggct ccaggaaagg ggctggagtt    180
gatcacatgc attggtacta gtcgtactac acatggtac gcgagctggg tgaaaggccg     240
attcaccatc tccagaacct cgaccacggt ggatctgaga atcagcagtc gacaatcga    300 ggacacggcc acctatttct gtgccagagg gagttatgct tataatcatg cgcttgctat    360
ctggggccca ggcaccctgg tcaccgtctc cttaggcaa cctaaggctc catcagtctt    420
cccactggcc cctgctgcg ggacacacc cagctccacg gtg                        463

<210> SEQ ID NO 8
<211> LENGTH: 469
<212> TYPE: DNA
<213> ORGANISM: Oryctolagus cuniculus

<400> SEQUENCE: 8
gcttctcctg gtcgctgtgc tcaaaggtgt ccagtgtcag gagcagcggg aggagtccgg     60
gggaggcctg gtcaagcctg gggcatccct gacactcacc tgccaagtct ctggattcga    120
cttcagttac tactactaca tgtgctgggt ccgccaggct ccaggaaagg ggctggagtg    180
gatcgggtgt tttactactg gtagtggtag tactgactac gcgaactggg cgaagagcca    240
attcaccatc tccgaaaccc cgtcgaccac gctgactcta caaatgacca gtctgacagc    300
cgcggacacg gccaccctatt tctgtgcgag atgcgttagt ggtaatagtt tctatgccat    360
ggacttctag ggcccaggga ccctcgtcac cgtctcttca gggcaaccta aggctccatc    420
agtcttccca ctggccccct gctgcgggga cacacccagc cccacggtg                469

<210> SEQ ID NO 9
<211> LENGTH: 466
<212> TYPE: DNA
<213> ORGANISM: Oryctolagus cuniculus

<400> SEQUENCE: 9
gcttctcctg gtcgctgtgc tcaaaggtgt ccagtgtcag tcgttggagg agtccggggg     60
aggcctggtc agcctgagg gatccctgac actcacctgt acagcctctg gattctcctt    120
cagtagctac tactacatgt gctgggtccg ccaggctcca gggaagggc ctgagtggat    180 cggatgtttt actactggca gtgagaccac tgactacgcg aactgggcga gagccgatt    240 caccatctcc aaaacctcgt cgaccacggt gactctacac atgaccagtc tgacagccgc    300
ggacacggcc acctatttct gtgcgagatg cgtgcctggt aatagtttct acgccatgga    360
```

| | |
|---|---|
| cctctggggc ccagggaccc tcgtcaccgt ctcttcaggg caacctaagg ctccatcagt | 420 |
| cttcccactg gcccctgct gcggggacac acccagctcc acggtg | 466 |

<210> SEQ ID NO 10
<211> LENGTH: 469
<212> TYPE: DNA
<213> ORGANISM: Oryctolagus cuniculus

<400> SEQUENCE: 10

| | |
|---|---|
| gcttctcctg gtcgctgtgc tcaaaggtgt ccagtgtcag tcgttggagg agtccggggg | 60 |
| agacctggtc aagcctgggg catccctgac actcacctgc acagcctctg gattctcctt | 120 |
| cagtaacggc tactacatgt gctgggtccg ccaggctcca gggaaggggc tggaatggat | 180 |
| cgcatgcatt tatgctggtg atagtggtcg cacttactac gcgcgctggg cgaaagaccg | 240 |
| agtcaccatc tccaaagtct cgtcgaccac ggtgactctg catatgacca gtctgacagc | 300 |
| cgcggacacg gccacctatt tctgtgcgag aagtggtcgt atgaatcctt atacatactt | 360 |
| caccttgtgg ggcccaggca ccctggtcac cgtctcctca gggcaaccta aggctccatc | 420 |
| agtcttccca ctggccccct gctgcgggga cacacccagc tccacggtg | 469 |

<210> SEQ ID NO 11
<211> LENGTH: 469
<212> TYPE: DNA
<213> ORGANISM: Oryctolagus cuniculus

<400> SEQUENCE: 11

| | |
|---|---|
| gcttctcctg gtcgctgtgc tcaaaggtgt ccagtgtcag tcgttggagg ggtccggggg | 60 |
| agacctggtc aagcctgggg cctccctcac actcacctgc aaagtctctg gattctcctt | 120 |
| cagtagcggc tactacatgt gctgggtccg ccaggctcca gggaaggggc tggagtggat | 180 |
| cgcatgcatt tatgctggta gtagtggtag tacttactac gcgaactggg cgaaaggccg | 240 |
| attcaccatc tccaaaacct cgtcgaccac ggtgactctg caaatgacca gtctgacagc | 300 |
| cgcggacacg gccacatatt tctgtgcgag aggtggtcgt tataatcctt atacatactt | 360 |
| cacctttggg ggcccaggca ccctggtcac cgtctcctca gggcaaccta aggctccatc | 420 |
| agtcttccca ctggccccct gctgcgggga cacacccagc tccacggtg | 469 |

<210> SEQ ID NO 12
<211> LENGTH: 682
<212> TYPE: DNA
<213> ORGANISM: Oryctolagus cuniculus

<400> SEQUENCE: 12

| | |
|---|---|
| tcagctgctg gggctcctgc tgctctggct cccaggtgcc agatgtgcat tcgaattgac | 60 |
| ccagactcca tcctccgtgt ctgcagctgt gggagacaca gtcaccatca gtgccaggc | 120 |
| cagtcagagc attagtagct acttagcctg gtatcagcag aaaccagggc agcctcccaa | 180 |
| gctcctgatc tacaaggcat ccactctggc atctggggtc ccatcgcggt tcaaaggcag | 240 |
| tagatctggg acagagttca ctctcaccat cagcgacctg gagtgtaccg atgctgccac | 300 |
| ttactactgt caaggtggtt attacagaag tagtagtgat tatactaatg ctttcggcgg | 360 |
| agggaccgag gtggtcgtca aggtgatcca gttgcacct actgtcctca tcttcccacc | 420 |
| atctgctgat cttgtggcaa ctggaacagt caccatcgtg tgtgtggcga ataaatactt | 480 |
| tcccgatgtc accgtcacct gggaggtgga tggcaccacc caaacaactg gcatcgagaa | 540 |
| cagtaaaaca ccgcagaatt ctgcagattg tacctacaac ctcagcagca ctctgacact | 600 | gaccagcaca cagtacaaca gccacaaaga gtacacctgc aaggtgaccc agggcacgac    660 ctcagtcgtc cagagcttca at                                             682

<210> SEQ ID NO 13
<211> LENGTH: 682
<212> TYPE: DNA
<213> ORGANISM: Oryctolagus cuniculus

<400> SEQUENCE: 13
tcagctgctg gggctcctgc tgctctggct cccaggtgcc agatgtgcat tcgagttgac    60
ccagactcca tcctccgtgg aggcagctgt gggaggcaca gtcaccatca agtgccaggc   120
cagtgagagc attggtagct acttagcctg gtatcagcag aaaccagggc agcctcccaa   180
gctcctgatc tacatggcag ccactctggc atctggggtc ccatcacggt ttaaaggcag   240
gagatctggg acagacttca ctctcaccat cagcgacctg gagtgtgccg atgctgccac   300
ttactactgt caaggcggtt attaccgtag tagtaatgat gttgccaatg ctttcggcgg   360
agggactgag gtggtcgtca aggtgatcc agttgcacct actgtcctca tcttcccacc   420
atctgctgat cttgtggcaa ctggaacagt caccatcgtg tgtgtggcga ataaatactt   480
tcccgatgtc accgtcacct gggaggtgga tggcaccacc caaacaactg gcatcgagaa   540
cagtaaaaca ccgcagaatt ctgcagattg tacctacaac ctcagcagca ctctgacact   600
gaccagcaca cagtacaaca gccacaaaga gtacacctgc aaggtgaccc agggcacgac   660
ctcagtcgtc cagagcttca at                                             682

<210> SEQ ID NO 14
<211> LENGTH: 688
<212> TYPE: DNA
<213> ORGANISM: Oryctolagus cuniculus

<400> SEQUENCE: 14
tcagctgctg gggctcctgc tgctctggct cccaggtgcc agatgtgccg aagtagtgat    60
gacccagact ccagcctccg tggaggcagc tgtgggaggc acagtcacca tcaagtgcca   120
ggccagtcag aggtttgaca ccaatttagc ctggtatcag cagaaaccag gcagcctcc   180 caagctcctg atctattctg catccactgt ggcatctggg gtcccatcgc ggttcaaagg   240
cagtggatct gggacacagt tcgctctcac catcagcgac ctgagtgtg ccgatgctgt   300 cacttactac tgtcaaggct attatgatag tagtaatagt ggtggtgatt cgaatgcttt   360
cggcggaggg accgaggtgg tcgtcaaagg tgatccagtt gcacctactg tcctcatctt   420
cccaccatct gctgatcttg tggcaactgg aacagtcacc atcgtgtgtg tggcgaataa   480
atactttccc gatgtcaccg tcacctggga ggtggatggc accacccaaa caactggcat   540
cgagaacagt aaaacaccgc agaattctgc agattgtacc tacaacctca gcagcactct   600
gacactgacc agcacacagt acaacagcca caaagagtac acctgcaagg tgacccaggg   660
cacgacctca gtcgtccaga gcttcaat                                       688

<210> SEQ ID NO 15
<211> LENGTH: 688
<212> TYPE: DNA
<213> ORGANISM: Oryctolagus cuniculus

<400> SEQUENCE: 15
tcagctgctg gggctcctgc tgctctggct cccaggtgcc agatgtgccg aagtagtgat    60

```
gacccagact ccagcctccg tggaggcagc tgtgggaggc acagtcacca tcaagtgcca    120
ggccagtcag agtattgata gtaatttagc ctggtatcag cagaaaccag ggcagcctcc    180
caagctcctg atctatggtg catccactct ggcatctggg gtcccatcgc ggttcaaagg    240
cagtggatct gggacacagt tcactctcac catcagcgac ctggagtgtg ccgatgctgc    300
cacttactac tgtcaaggct attttgatag tagtaatact ggtagtgatt cgaattcttt    360
cggcggaggg accgaggtgg tcgtcaaagg tgatccagtt gcacctactg tcctcatctt    420
cccaccatct gctgatcttg tggcaactgg aacagtcacc atcgtgtgtg tggcgaataa    480
atactttccc gatgtcaccg tcacctggga ggtggatggc accacccaaa caactggcat    540
cgagaacagt aaaacaccgc agaattctgc agattgtacc tacaacctca gcagcactct    600
gacactgacc agcacacagt acaacagcca caaagagtac acctgcaagg tgacccaggg    660
cacgacctca gtcgtccaga gcttcaat                                      688

<210> SEQ ID NO 16
<211> LENGTH: 682
<212> TYPE: DNA
<213> ORGANISM: Oryctolagus cuniculus

<400> SEQUENCE: 16
tcagctgctg gggctcctgc tgctctggct cccaggtgcc agatgtgccg aagtagtgat     60
gacccagact ccagcctccg tggaggcagt tgtgggaggc acagtcacca tcaagtgcca    120
ggccagtcag agcattggta gtgccttatc ctggtatcag cagaaacctg ggcagcctcc    180
caagctcctg atctatggta catccactct ggcatctggg gtcccatcgc ggttcaaagg    240
cagtggatct gggacacagt tcactctcac catcagcgac ctcgagtgtg ccgatgctgc    300
cacttactac tgtcaaagta attatgttag tggtactaat tatcatcatg gtttcggcgg    360
agggaccgag gtggtcgtca aaggtgatcc agttgcacct actgtcctca tcttcccacc    420
atctgctgat cttgtggcaa ctggaacagt caccatcgtg tgtgtggcga ataaatactt    480
tcccgatgtc accgtcacct gggaggtgga tgcaccacc caaacaactg gcatcgagaa    540
cagtaaaaca ccgcagaatt ctgcagattg tacctacaac ctcagcagca ctctgacact    600
gaccagcaca cagtacaaca gccacaaaga gtacacctgc aaggtgaccc agggcacgac    660
ctcagtcgtc cagagcttca at                                            682

<210> SEQ ID NO 17
<211> LENGTH: 682
<212> TYPE: DNA
<213> ORGANISM: Oryctolagus cuniculus

<400> SEQUENCE: 17
tcagctgctg ggtctcctgc tgctctggct cccaggtgcc agatgtgatg ttgtgatgac     60
ccagactcca gcctccgtgg aggcggctgt gggaggcaca gtcaccatca attgccaggc    120
cagtgaagat attaatagat acttagcctg gtatcagcag aaaccagggc agcctcccaa    180
gctcctgatc tacagggcat ccactctgga atctggggtc catcgcggt tcaaaggcag    240 tagatctggg acagagttca ctctcaccat cagcgacctg gagtgtgccg atgctgccac    300
ttactactgt cagagcaatt attatatgag tgtcagtaat tatgaaaatg ctttcggcgg    360
agggaccgag gtggtcgtca aaggtgatcc agttgcacct actgtcctca tcttcccacc    420
atctgctgat cttgtggcaa ctggaacagt caccatcgtg tgtgtggcga ataaatactt    480
tcccgatgtc accgtcacct gggaggtgga tgcaccacc caaacaactg gcatcgagaa    540
```

```
cagtaaaaca ccgcggaatt ctgcagattg tacctacaac ctcagcagca ctctgacact    600
gaccagcaca cagtacaaca gccacaaaga gtacacctgc aaggtgaccc agggcacgac    660
ctcagtcgtc cagagcttca at                                            682
```

<210> SEQ ID NO 18
<211> LENGTH: 676
<212> TYPE: DNA
<213> ORGANISM: Oryctolagus cuniculus

<400> SEQUENCE: 18

```
tcagctgctg gggctcctgc tgctctggct cccaggtgcc agatgtgatg ttgtgatgac     60
ccagactcca gcctccgtgt ctgaacctgt gggaggcaca gtcaccatca gtgccaggc    120 cagtgagaat atctacaggt cttagcctg catcagcag aaaccagggc agcctcccaa     180
gctcccgatc tatggtgcat ctactctggc atctggggtc ccatcgcggt tcaaaggcag    240
tggatctggg acagagttca ctctcaccat cagcggcctg gagtgtgacg atgctgccac    300
ttattactgt caaaatattt atgttagtga tggtgatggc aatgctttcg gcggcgggac    360
cgaggtggtc gtcaaaggtg atccagttgc acctactgtc ctcatcttcc caccatctgc    420
tgatcttgtg caactggaa cagtcaccat cgtgtgtgtg gcgaataaat actttcccga    480
tgtcaccgtc acctgggagg tggatggcac acccaaaca actggcatcg agaacagtaa    540
aacaccgcag aattctgcag attgtaccta caacctcagc agcactctga cactgaccag    600
cacacagtac aacagccaca agagtacac ctgcaaggtg acccagggca cgacctcagt    660
cgtccagagc ttcaat                                                    676
```

<210> SEQ ID NO 19
<211> LENGTH: 682
<212> TYPE: DNA
<213> ORGANISM: Oryctolagus cuniculus

<400> SEQUENCE: 19

```
tcagctgctg gggctcctgc tgctctggct cccaggtgcc agatgtgccg tcgtgctgac     60
ccagactcca tcccccgtgt ctggacctgt gggaggcaca gtcaccatca gtgccaggc    120 cagtcagagc attagcaatg cattagcctg gtatcagcag aaaccagggc agcctcccaa    180
gctcctgatc ttttttgcat ccactctggc atctggggtc ccatcgcggt tcagcggcag    240
tggatctggg acagacttca ctctcaccat cagcgacctg gagtgtgccg atgctgccac    300
ttactactgt caaagttact attatagtag ttatagtgct gaaagtaatg ctttcggcgg    360
agggaccgag gtggtcgtca aaggtgatcc agttgtacct actgtcctca tcttcccacc    420
atctgctgat cttgtggcaa ctggaacagt caccatcgtg tgtggcga ataaatactt    480 tcccgatgtc accgtcacct gggaggtgga tggcaccacc caaacaactg gcatcgagaa    540
cagtaaaaca ccgcagaatt ctgcagattg tacctacaac ctcagcagca ctctgacact    600
gaccagcaca cagtacaaca gccacaaaga gtacacctgc aaggtgaccc agggcacgac    660
ctcagtcgtc cagagcttca at                                            682
```

<210> SEQ ID NO 20
<211> LENGTH: 682
<212> TYPE: DNA
<213> ORGANISM: Oryctolagus cuniculus

<400> SEQUENCE: 20

| | |
|---|---:|
| tcagctgctg gggctcctgc tgctctggct cccaggtgcc acatttgctc aagtggtgac | 60 |
| ccaggctgaa tcgcccgtgt ctgcacctgt gggaggcaca gtcaccatca attgccaggc | 120 |
| cagtcagagt cttgatgatg acaactggtt atcctggtat cagcagaaac cagggcagcc | 180 |
| tcccaagctc ctgatctacg aagcatccaa actggcatct ggggtcccat cgcggttcaa | 240 |
| aggcagtgga tctgggacac agttcactct caccctcacc gacatgcagt gtgacgatgc | 300 |
| tgccacttac tactgtcaag ccacttatta tagtagtggt tggtacaatg gtttcggcgg | 360 |
| agggaccgag gtggtcgtca aggtgatcc agttgcacct actgtcctca tcttcccacc | 420 |
| atctgctgat cttgtggcaa ctggaacagt caccatcgtg tgtgtggcga ataaatactt | 480 |
| tcccgatgtc accgtcacct gggaggtgga tggcaccacc caaacaactg gcatcgagaa | 540 |
| cagtaaaaca ccgcagaatt ctgcagattg tacctacaac ctcagcagca ctctgacact | 600 |
| gaccagcaca cagtacaaca gccacaaaga gtacacctgc aaggtgaccc agggcacgac | 660 |
| ctcagtcgtc cagagcttca at | 682 |

<210> SEQ ID NO 21
<211> LENGTH: 679
<212> TYPE: DNA
<213> ORGANISM: Oryctolagus cuniculus

<400> SEQUENCE: 21

| | |
|---|---:|
| tcagctgctg gggctcctgc tgctctggct cccaggtgcc agatgtgccg tcgtgatgac | 60 |
| ccagactgca tccccgtgt ctgcagctgt gggaggcaca gtcaccatca attgccaggc | 120 |
| cagtcagagt attagtagta gctacttatc tggtatcag cagaaaccag ggcagcctcc | 180 |
| caagctcctg atctacaagg cttccactct ggcatctggg gtcccatcgc ggttcaaagg | 240 |
| cagtggatct gggacagagt acactcttac catcagcgat gtgcagtgtg acgatgctgg | 300 |
| cacttactac tgtctatacg gttcttatag tagtactagt ggcaatgctt tcggcggagg | 360 |
| gaccgaggtg gtggtcaaag gtgatccagt tgcacctact gtcctcatct tcccaccagc | 420 |
| tgctgatcag gtggcaactg gaacagtcat catcgtgtgt gtggcgaata atactttcc | 480 |
| cgatgtcacc gtcacctggg aggtggatgg caccacccaa caactggca tcgagaacag | 540 |
| taaaacaccg cagaattctg cagattgtac ctacaacctc agcagcactc tgacactgac | 600 |
| cagcacacag tacaacagcc acaaagagta cacctgcaag gtgacccagg gcacgacctc | 660 |
| agtcgtccag agcttcaat | 679 |

<210> SEQ ID NO 22
<211> LENGTH: 682
<212> TYPE: DNA
<213> ORGANISM: Oryctolagus cuniculus

<400> SEQUENCE: 22

| | |
|---|---:|
| tcagctgctg gggctcctgc tgctctggct cccaggtgcc acatttgcca tcgtgatgac | 60 |
| ccagactcca tcttccaagt ctgtccctgt gggagacaca gtcaccatca attgccaggc | 120 |
| cactgagagt gttatagta acaaccgctt agcctggtat tagcagaaac caggtcagcc | 180 |
| tcccaagctc ctgatctatc tggcatccac tctggcatct ggggtcccat cgcggttcaa | 240 |
| aggcagtgga tctgggacac agttcactct caccatcagc gatgtggtgt gtgacgatgc | 300 |
| tgccacttac tactgtcagg atatacaga tagaggtagt gatgctggtg ctttcggcgg | 360 |
| agggaccgag gtggtggtca aggtgatcc agttgcacct actgtcctca tcttcccacc | 420 |
| agctgctgat caggtggcaa ctggaacagt caccatcgtg tgtgtggcga ataaatactt | 480 |

-continued

```
tcccgatgtc accgtcacct gggaggtgga tggcaccacc caaacaactg gcatcgagaa        540
cagtaaaaca ccgcagaatt ctgcagattg tacctacaac ctcagcagca ctctgacact        600
gaccagcaca cagtacaaca gccacaaaga gtacacctgc aaggtgaccc agggcacgac        660
ctcagtcgtc cagagcttca at                                                682
```

FACS-BASED METHOD FOR OBTAINING AN ANTIBODY SEQUENCE

CROSS-REFERENCING

This application claims the benefit of U.S. provisional application Ser. No. 61/506,953, filed on Jul. 12, 2011, which application is incorporated by reference herein.

INTRODUCTION

Antibodies are proteins that bind a specific antigen. Generally, antibodies are specific for their targets, have the ability to mediate immune effector mechanisms, and have a long half-life in serum. Such properties make antibodies powerful therapeutics. Monoclonal antibodies are used therapeutically for the treatment of a variety of conditions including cancer, inflammation, and other diseases. There are currently over two dozen therapeutic antibody products on the market and hundreds in development.

There is a constant need for new antibodies and methods for making the same.

SUMMARY

In certain embodiments, the method may comprises: a) contacting a population of permeabilized, cross-linked antibody-producing cells with a labeled antigen or labeled antibody to produce a labeled sample in which cells that produce an antibody that specifically binds to said antigen or labeled antibody are intracellularly labeled; b) using FACS to isolate cells that are intracellularly labeled, thereby producing labeled cells; c) uncrosslinking said labeled cells to produce uncrosslinked cells; and d) amplifying heavy and light chain-encoding nucleic acid from individual uncrosslinked cells, thereby obtaining nucleic acid that encodes the variable domain of antibody that specifically binds to said antigen or labeled antibody.

In certain embodiments, the method can be performed without making hybridomas and, as such, the method provides a highly efficient alternative to conventional hybridoma-based methods for isolating antibody-encoding sequences. Further, in certain cases the method provides a means by which significant portion of the entire antibody repertoire of an animal can be screened to identify and clone the encoding nucleic acid of an antibody with desirable properties. After identification, the antibody may be tested in further assays, and, if it is suitable for use as a therapy, may be humanized, for example.

BRIEF DESCRIPTION OF THE DRAWINGS

The skilled artisan will understand that the drawings, described below, are for illustration purposes only. The drawings are not intended to limit the scope of the present teachings in any way.

Figure 8C:
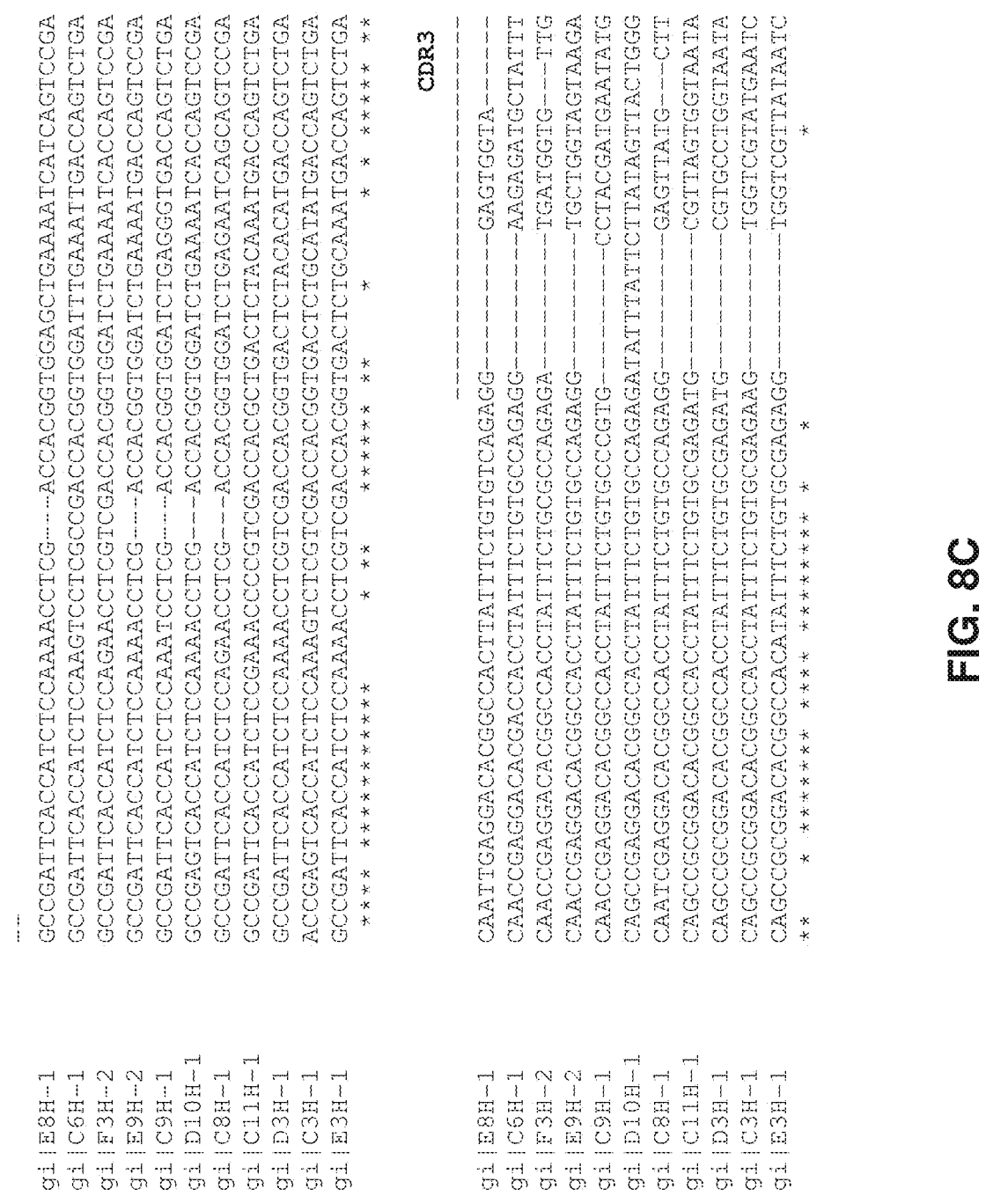

FIGS. 8A-8D show nucleotide sequences that encode the heavy chains for 11 antibodies (from top to bottom: SEQ ID NOS:1-11).

Figure 9C:
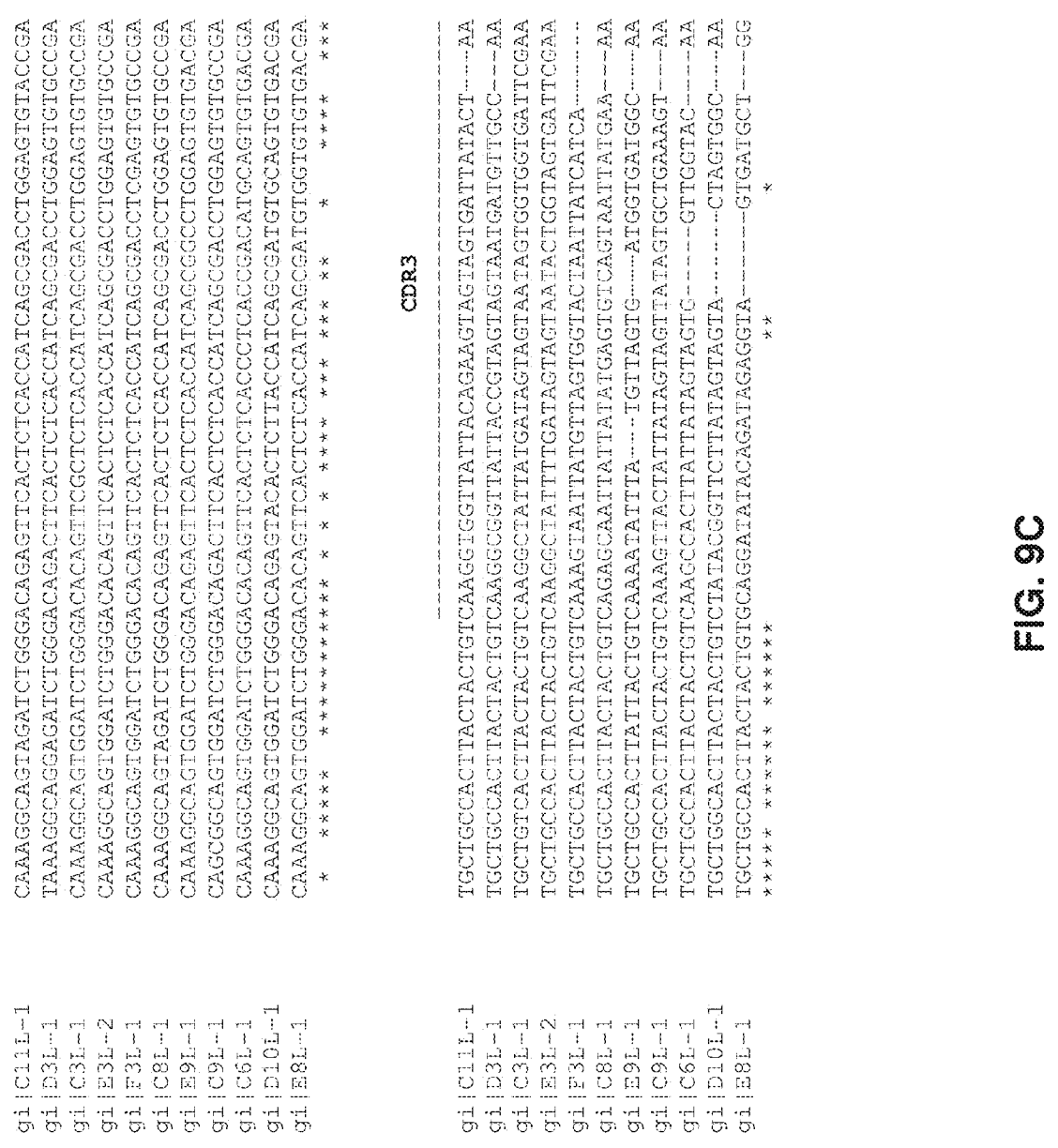

FIGS. 9A-9D show nucleotide sequences that encode the light chains for 11 antibodies (from top to bottom: SEQ ID NOS:12-22).

DEFINITIONS

Figure 1:
FIG. 1 schematically illustrates one embodiment of the method.
Figure 1:
Figure 1:
Figure 1:
Figure 1:

Before the present subject invention is described further, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an antibody" includes a plurality of such antibodies and reference to "a framework region" includes reference to one or more framework regions and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The term "nucleic acid" encompasses DNA, RNA, single stranded or double stranded and chemical modifications thereof. The terms "nucleic acid" and "polynucleotide" are used interchangeably herein.

The term "expression", as used herein, refers to the process by which a polypeptide is produced based on the nucleic acid sequence of a gene. The process includes both transcription and translation.

The term "expression cassette" refers to a nucleic acid construct capable of directing the expression of a gene/coding sequence of interest, which is operably linked to a promoter of the expression cassette. Such cassettes can be a linear nucleic acid or can be present in a "vector", "vector construct", "expression vector", or "gene transfer vector", in order to transfer the expression cassette into target cells. Thus, the term includes cloning and expression vehicles, as well as viral vectors.

The term "operably linked" refers to an arrangement of elements wherein the components so described are configured so as to perform their usual function. Thus, a given signal peptide that is operably linked to a polypeptide directs the secretion of the polypeptide from a cell. In the case of a promoter, a promoter that is operably linked to a coding sequence will direct the expression of the coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

The term "plurality" refers to more than 1, for example more than 2, more than about 5, more than about 10, more than about 20, more than about 50, more than about 100, more than about 200, more than about 500, more than about 1000, more than about 2000, more than about 5000, more than about 10,000, more than about 20,000, more than about 50,000, more than about 100,000, usually no more than about 200,000. A "population" contains a plurality of items.

The term "introduced" in the context of inserting a nucleic acid sequence into a cell, means "transfection", or 'transformation", or "transduction" and includes reference to the incorporation of a nucleic acid sequence into a eukaryotic or prokaryotic cell wherein the nucleic acid sequence may be present in the cell transiently or may be incorporated into the genome of the cell (e.g., chromosome, plasmid, plastid, or mitochondrial DNA), converted into an autonomous replicon.

The terms "antibody" and "immunoglobulin" are used interchangeably herein. These terms are well understood by those in the field, and refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized immunoglobulin polypeptides include the kappa and lambda light chains and the alpha, gamma ($IgG_1$, $IgG_2$, $IgG_3$, $IgG_4$), delta, epsilon and mu heavy chains or equivalents in other species. Full-length immunoglobulin "light chains" (of about 25 kDa or about 214 amino acids) comprise a variable region of about 110 amino acids at the $NH_2$-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies.

Antibodies may exist in a variety of other forms including, for example, Fv, Fab, and (Fab')$_2$, as well as bi-functional (i.e. bi-specific) hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed., 1984, and Hunkapiller and Hood, Nature, 323, 15-16, 1986).

An immunoglobulin light or heavy chain variable region consists of a framework region (FR) interrupted by three hypervariable regions, also called "complementarity determining regions" or "CDRs". The extent of the framework region and CDRs have been precisely defined (see, "Sequences of Proteins of Immunological Interest," E. Kabat et al., U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen.

The term "chimeric antibodies" refer to antibodies whose light and heavy chain genes have been constructed, typically by genetic engineering, from antibody variable and constant region genes belonging to different species. For example, the variable segments of the genes from a mouse monoclonal antibody may be joined to human constant segments, such as gamma 1 and gamma 3. An example of a therapeutic chimeric antibody is a hybrid protein composed of the variable or antigen-binding domain from a rabbit antibody and the constant or effector domain from a human antibody, although other mammalian species may be used.

The term "humanized antibody" or "humanized immunoglobulin" refers to a non-human (e.g., mouse or rabbit) antibody containing one or more amino acids (in a framework region, a constant region or a CDR, for example) that have been substituted with a correspondingly positioned amino acid from a human antibody. In general, humanized antibodies produce a reduced immune response in a human host, as compared to a non-humanized version of the same antibody.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones.

The term "natural" antibody refers to an antibody in which the heavy and light chains of the antibody have been made and paired by the immune system of a multi-cellular organism. Spleen, lymph nodes, bone marrow and blood are examples of tissues that contain cells that produce natural antibodies. For example, the antibodies produced by the antibody producing cells isolated from a first animal immunized with an antigen are natural antibodies. Natural antibodies contain naturally-paired heavy and light chains.

The terms "lineage-related antibodies", "clonally-related antibodies" and "antibodies that related by lineage" as well as grammatically-equivalent variants there of, are antibodies that are produced by cells that share a common B cell ancestor. Related antibodies produced by related antibody producing cells bind to the same epitope of an antigen and are typically very similar in sequence, particularly in their L3 and H3 CDRs. Both the H3 and L3 CDRs of lineage-related antibodies have an identical length and a near identical sequence (i.e., differ by up to 5, i.e., 0, 1, 2, 3, 4 or 5 residues). In certain cases, the B cell ancestor contains a genome having a rearranged light chain VJC region and a rearranged heavy chain VDJC region, and produces an antibody that has not yet undergone affinity maturation. "Naïve" or "virgin" B cells present in spleen tissue, are exemplary B cell common ancestors. Related antibodies are related via a common antibody ancestor, e.g., the antibody produced in the naïve B cell ancestor. The term "related antibodies" is not intended to describe a group of antibodies that are not produced by cells that arise from the same ancestor B-cell. A "lineage group" contains a group of antibodies that are related to one another by lineage.

The terms "treating" or "treatment" of a condition or disease refer to providing a clinical benefit to a subject, and include: (1) preventing at least one symptom of the conditions, i.e., causing a clinical symptom to not significantly develop in a mammal that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms.

The term "intact cells" includes cells that have been fixed and/or permeabilized. Cells that have been lysed and/or sectioned or not intact cells. Western blots and assays in which either the proteins of a cell lysate or an antibody are affixed to a solid support (e.g., ELISAs) do not involve intact cells.

The term "blood sample" or grammatical equivalents thereof refer to a sample of whole blood or a sub-population of cells in whole blood. Sub-populations of cells in whole blood include platelets, red blood cells (erythrocytes), platelets and white blood cells (i.e., peripheral blood leukocytes, which are made up of neutrophils, lymphocytes, eosinophils, basophils and monocytes). These five types of white blood cells can be further divided into two groups, granulocytes (which are also known as polymorphonuclear leukeocytes and include neutrophils, eosinophils and basophils) and mononuclear leukocytes (which include monocytes and lymphocytes). Lymphocytes can be further divided into T cells, B cells and NK cells. Peripheral blood cells are found in the circulating pool of blood and not sequestered within the lymphatic system, spleen, liver, or bone marrow.

The term "capture agent" refers to an agent that binds a target molecule through an interaction that is sufficient to permit the agent to bind and concentrate the target molecule from a homogeneous mixture of different molecules. The binding interaction is typically mediated by an affinity region of the capture agent. Typical capture agents include any moiety that can specifically bind to a target molecule. In certain embodiments, a polypeptide, e.g., an antibody, may be employed.

Capture agents, e.g., antibodies, "specifically bind" a target molecule. Accordingly, the term "capture agent" refers to a molecule or a multi-molecular complex which can specifically bind a target molecule, e.g., a phosphorylated polypeptide, with a dissociation constant ($K_D$) of less than about $10^{-6}$ M (e.g., less than about $10^{-7}$ M, less than about $10^{-8}$M, less than about $10^{-9}$M, less than about $10^{-10}$ M, less than about $10^{-11}$ M, less than about $10^{-12}$ M, to as low as $10^{-16}$ M) without significantly binding to other molecules. The term "specific binding" refers to the ability of a capture agent to preferentially bind to a particular target molecule that is present in a homogeneous mixture of different target molecule. A specific binding interaction will discriminate between desirable (e.g., phosphorylated) and undesirable (e.g., unphosphorylated) target molecules in a sample, typically more than about 10 to 100-fold or more (e.g., more than about 1000- or 10,000-fold).

As used herein, the term "fluorescence activated cell sorting" or "FACS" refers to a method by which the individual cells of a sample are analyzed and sorted according to their optical properties (e.g., light absorbance, light scattering and fluorescence properties, etc.) as they pass in a narrow stream in single file through a laser beam.

The term "mixture", as used herein, refers to a combination of elements, e.g., cells, that are interspersed and not in any particular order. A mixture is homogeneous and not spatially separated into its different constituents. Examples of mixtures of elements include a number of different cells that are present in the same aqueous solution in a spatially undressed manner.

"Isolated" or "purified" refers to isolation of a substance (compound, polynucleotide, protein, polypeptide, polypeptide composition) such that the substance comprises a significant percent (e.g., greater than 2%, greater than 5%, greater than 10%, greater than 20%, greater than 50%, or more, usually up to about 90%-100%) of the sample in which it resides. A substantially purified component comprises at least 50%, 80%-85%, or 90-95% of the sample.

The term "assessing" includes any form of measurement, and includes determining if an element is present or not. The terms "determining", "measuring", "evaluating", "assessing" and "assaying" are used interchangeably and may include quantitative and/or qualitative determinations. Assessing may be relative or absolute. "Assessing the presence of" includes determining the amount of something present, and/or determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

As used herein, the term "in vivo" refers to the body of a whole living organism, e.g., a living mammal.

As used herein, the term "ex vivo" refers to living tissue that has been removed from the body of a whole living organism, e.g., a living mammal. A sample of blood that has been drawn from a mammal and contains living cells is an example of an ex vivo sample.

As used herein, the term "in vitro" refers to cells that have been grown in culture.

As used herein, the term "cross-linking" in the context of crosslinking cells refers to the cross-linking of the intracellular contents of cells, rather than the cross-linking of cells to one another. "Cross-linking and "fixing" can be used interchangeably.

DETAILED DESCRIPTION OF EXEMPLARY EMBODIMENTS

One embodiment of the subject method is schematically illustrated in FIG. 1. With reference to FIG. 1, the first step of the method may comprise: contacting a population of cross-linked (i.e., fixed) permeabilized, antibody-producing cells (e.g., lymphocytes or splenocytes, etc.) with a labeled antigen to produce a labeled sample. In this step, only cells that produce an antibody that specifically binds to the labeled antigen are intracellularly labeled. In the next step of the method, fluorescence activated cell sorting (FACS) is employed to isolate cells that are labeled from those that are not labeled to produce labeled cells. The labeled cells are then uncrosslinked, and nucleic acid encoding the heavy and light chain variable domains can be amplified from individual uncrosslinked cells, e.g., by PCR. Nucleic acid that encodes both the heavy and light chain variable domains of a naturally paired antibody that specifically binds to the antigen are thereby obtained.

In any embodiment described herein, a labeled antibody (e.g., an antibody that binds to a region that is conserved region in antibodies such as an anti-Fc antibody) can be employed instead of the labeled antigen. In these embodiments, the isolation of the cells can be timed (relative to exposure to an antigen), to provide an antibody-producing cell population is naturally highly enriched for antigen specific antibody producing cells. Therefore, in these embodiments, cells labeled solely with a large amount of anti-IgG Fc could also be useful in isolating antigen specific antibody secreting cells. The isolated antibodies may be later screened for antigen specificity using recombinant expression.

Antibody-Producing Cells

An antibody-producing cell is a cell that produces antibodies. Such cells are typically cells involved in a mammalian immune response (such as a B-lymphocyte and plasma cells) and produce immunoglobulin heavy and light chains that have been "naturally paired" by the immune system of the host. These cells may in certain cases secrete antibodies or maintain antibodies on the surface of the cell without secretion into the cellular environment. Antibody producing cells include hybridoma cells that express antibodies. In one embodiment, permeabilized, cross-linked peripheral blood leukocytes, or a sub-population thereof, e.g. lymphocytes, are employed.

An antibody-producing cell may be obtained from an animal which has been immunized with a selected antigen, e.g., a peptide, an animal which has not been immunized with a selected antigen (e.g., an animal having an autoimmune disease) or which has developed an immune response to an antigen as a result of disease or infection. Animals may be immunized with a selected antigen using any of the techniques well known in the art suitable for generating an immune response (see Handbook of Experimental Immunology D. M. Weir (ed.), Vol 4, Blackwell Scientific Publishers, Oxford, England, 1986). Within the context of the present invention, the phrase "selected antigen" includes any substance to which an antibody may be made, including, among others, proteins, carbohydrates, inorganic or organic molecules, transition state analogs that resemble intermediates in an enzymatic process, nucleic acids, cells, including cancer cells, cell extracts, pathogens, including living or attenuated viruses, bacteria, vaccines and the like. As will be appreciated by one of ordinary skill in the art, antigens which are of low immunogenicity may be accompanied with an adjuvant or hapten in order to increase the immune response (for example, complete or incomplete Freund's adjuvant) or with a carrier such as keyhole limpet hemocyanin (KLH).

Many warm-blooded animals, in particular mammals such as humans, rabbits, mice, rats, sheep, cows or pigs and ayes such as chickens and turkeys, may be used in order to obtain antibody-forming cells. Procedures for immunizing animals are well known in the art, and are described in Harlow et al., (*Antibodies: A Laboratory Manual*, First Edition (1988) Cold Spring Harbor, N.Y.). Antibody-producing cells may also be obtained from a subject that has generated the cells during the course of a selected disease or condition. For instance, antibody-producing cells from a human with a disease of unknown cause, such as rheumatoid arthritis, may be obtained and used in an effort to identify antibodies which have an effect on the disease process or which may lead to identification of an etiological agent or body component that is involved in the cause of the disease. Similarly, antibody-producing cells may be obtained from subjects with disease due to known etiological agents such as malaria or AIDS. These antibody-producing cells may be derived from the blood, lymph nodes or bone marrow, as well as from other diseased or normal tissues. Antibody-producing cells may also be prepared from blood collected with an anticoagulant such as heparin or EDTA. The antibody-producing cells may be further separated from erythrocytes and polymorphs using standard procedures such as centrifugation with Ficoll-Hypaque (Pharmacia, Uppsula, Sweden). Antibody-producing cells may also be prepared from solid tissues such as lymph nodes, tumors or spleen by dissociation with enzymes such as collagenase and trypsin in the presence of EDTA.

Antibody-producing cells may also be obtained by culture techniques such as in vitro immunization. Examples of such methods are described (Reading in Methods in Enzymology (21:18-33 J. J. Langone, H. H. van Vunakis (eds.), Academic Press Inc., N.Y.; 1986). Briefly, a source of antibody-producing cells, such as a suspension of spleen or lymph node cells, or peripheral blood mononuclear cells are cultured in medium such as RPMI 1640 with 10% fetal bovine serum and a source of the substance against which it is desired to develop antibodies. This medium may be additionally supplemented with amounts of substances known to enhance antibody-forming cell activation and proliferation such as lipopolysaccharide or its derivatives or other bacterial adjuvants or cytokines such as IL-1, IL-2, IL-4, IL-5, IL-6, GM-CSF, and IFN-.gamma. To enhance immunogenicity, the selected antigen may be coupled to the surface of cells, for example, spleen cells, by conventional techniques such as the use of biotin/avidin.

Once a suitable animal containing an antibody-producing cell has been identified or produced, spleen, lymph node or bone marrow tissue may be removed, and a cell suspension of antibody-producing cells may be prepared using, e.g., techniques well known in the art. In most embodiments, this suspension is a single cell suspension, techniques for the preparation of which are well known in the art, e.g., Harlow et al., (*Antibodies: A Laboratory Manual*, First Edition (1988) Cold Spring Harbor, N.Y.).

Antibody-producing cells may be enriched from the single cell suspension by methods based upon the size or density of the antibody-forming cells relative to other cells. An example of the use of Percoll to separate cells according to density is described by van Mourik and W. P. Zeizlmaker in Methods in Enzymology 121:174-182 (J. J. Langone, H. H. van Vunakis (eds.), Academic Press Inc., N.Y.). Gradients of varying density of solutions of bovine serum albumin can also be used to separate cells according to density. (See N. Moav and T. N. Harris, J. Immunol 105:1512, 1970; see also Raid, D. J. in SELECTED METHODS IN CELLULAR IMMUNOLOGY, B. Mishell and S. Shiigi (eds.), W. H. Freeman and Co., San Francisco, 1987). Antibody-producing cells may also be enriched and plated using other methods.

Intracellular Labeling and FACS

While the exact protocol of the intracellular labeling steps may vary, they generally involve: a) cross-linking antibody producing cells so that the contents of the cells stay intact during subsequent manipulations, b) permeabilizing the cross-linked cells, and then c) labeling the permeabilized, cross-linked cells using a labeled antigen. The labeled antigen passes into the cells and is bound by antibody protein that is in the interior of the cell. Only antibody producing cells that contain an antibody that specifically recognizes the antigen will be labeled.

Exemplary methods by which cells can be intracellularly labeled using labeled antibody may be adapted from variety of publications, including: Lazarus et al (Cytometry. 1998 32:206-13), Sartor et al (Cytometry. 1994 18:119-22), Gadol et al (Cytometry 1994 15:359-70) and Far et al (Cytometry.

1994 15:327-34), which described methods by which intracellular proteins are labeled with fluorescent antibodies and are incorporated by reference for disclosure of these methods. Methods for performing flow cytometry on intracellularly labeled proteins are known (see, e.g., Krutzik Cytometry 2003 55: 61-70; Fleisher Clin. Immunol. 1999 90: 425-430; and Krutzik J. Immunol. 2005 175, 2357-2365). Kits for intracellularly labeling cells for FACS analysis include the INTRACYTE™ intracellular FACS kit by Orion BioSolutions, Inc (Vista, Calif.), the INTRASURE™ or FASTIMMUNE™ kits by Becton Dickinson (Franklin Lakes, N.J.) and the CYTOFIX™ or CYTOPERM™ Plus kits by PharMingen (San Diego, Calif.). Depending on the method employed, the red blood cells of the sample may be lysed prior to permeablizing and labeling of the white blood cells. Such lysis techniques may be adapted from those commonly employed in blood analysis.

The cross-linking agent used for fixing the cells should be reversible. In a particular embodiment, an aldehyde crosslinking agent, e.g., formaldehyde, may be employed. In a particular case, formaldehyde may be used as 10% neutral buffered formalin (NBF), that is approximately 3.7% formaldehyde in phosphate buffered saline. Because formaldehyde is a gas at room temperature, formalin-formaldehyde gas dissolved in water (~37% w/v) is used when making the former fixative. Paraformaldehyde is a polymerised form of formaldehyde, usually obtained as a fine white powder, which depolymerises back to formalin when heated. Formaldehyde fixes tissue by primarily cross-linking the protein in a cell, via lysine residues.

Another aldehyde that may be employed for fixation is glutaraldehyde. Glutaraldehyde operates in a similar way to formaldehyde by causing deformation of the alpha-helix structures in proteins. However, glutaraldehyde is a larger molecule, and so its rate of diffusion across membranes is slower than formaldehyde. One of the advantages of glutaraldehyde fixation is that it may offer a more rigid or tightly linked fixed product—its greater length and two aldehyde groups allow it to 'bridge' and link more distant pairs of protein molecules. Some fixation protocols call for a combination of formaldehyde and glutaraldehyde so that their respective strengths complement one another.

Aldehyde cross-links can be reversed, e.g., by altering the pH, by dilution with an aqueous solution, e.g., water, or by simply by heating the crosslinked sample.

Permeabilization of cells can be achieved using any number of reagents that are well known in the art, including, but not limited to, digitonin, saponin, triton, tween, methanol, ethanol, acetone (or other detergents and alcohols) and the like. Indeed, reagents and kits for permeabilization and fixation of cells for flow cytometric analysis are available from commercial vendors (e.g., CytoFix/CytoPerm buffer; PharMingen, La Jolla, Calif.).

Methods for conjugating a fluorescent label to protein, e.g., to a peptide, are well known. In alternative embodiments, the antigen may be labeled indirectly using a secondary antibody that binds to the antigen (without disrupting the binding of the antibody of the antibody-producing cells).

In particular cases, in addition to being labeled with the antigen, the cells may be distinguishably labeled with other probes, including, but not limited to, antibodies to cell surface markers that distinguish one cell type from another CD19 and CD21, etc. In another embodiment, the cells may be additionally labeled with a second antibody that binds non-specifically to antibodies, e.g., to the Fc region of an antibody. In this embodiment, a labeled anti-IgG Fc antibody may be employed.

Once labeled, the intracellularly labeled cells may be isolated by FACS. In some embodiments, the FACS machine may isolate labeled cells singly (i.e., as single cells). In other embodiments, the labeled cells may be isolated as a mixed population, and then diluted into single cells after FACS.

In embodiments in which the cell is labeled with a plurality of different labels, the cells may be selected using a plurality of different properties. For example, if the cell is labeled with a labeled antigen and a labeled anti-IgG Fc antibody, the cell may be isolated as having a high intracellular IgG Fc content in addition to containing antibodies that bind to the labeled antigen.

The general principles of fluorescence activated cell sorting, including methods by which single cell suspensions can be made, methods by which cells can be labeled using, e.g., fluorescently labeled probes, methods by which cells can be separated from one another, as well as hardware that can be employed in flow cytometry, including flow cells, reagents, and computer control systems are known and are reviewed in a variety of publications, including, but not limited to: Orfao et al (Clin. Biochem. 1996 29:5-9), Johnson et al (Curr. Pharm. Biotechnol. 2007 8:133-9), Tung et al (Clin. Lab. Med. 2007 27:453-68), and Dainiak et al (Adv. Biochem. Eng. Biotechnol. 2007 106: 1-18), which publications are incorporated by reference herein for disclosure of those methods and hardware.

Single Cell PCR

Prior to amplifying the antibody-encoding sequences, the labeled cells should be uncrosslinked, i.e., the crosslinking should be reversed. This step can be done using many different methods. However, because the cells are going to be subjected to PCR, in some embodiments the cells may heated (e.g., an extended period of time at least 50° C. such as 3-10 hrs at 65° C. or 15-60 mins at above 90° C.).

Sequences encoding heavy and light chains may be amplified from individual cells using techniques well known in the art, such as polymerase chain reaction (PCR). The sequences may be amplified from genomic DNA, or from mRNA (by RT-PCR). In one embodiment, cDNA segments encoding the variable domain of the antibody are exponentially amplified by performing sequential reactions with a DNA polymerase. The reaction is primed by a 5' and a 3' DNA primer. In some embodiments, the 3' antisense primer corresponding to a DNA sequence in the constant (or joining) region of the immunoglobulin chain and the 5' primer (or panel of related primers) corresponding to a DNA sequence in the variable region of the immunoglobulin chain. This combination of oligonucleotide primers has been used in the PCR amplification of murine immunoglobulin cDNAs of unknown sequence (see Sastry et at., Proc Natl. Acad. Sci. 86:5728-5732, 1989 and Orlandi et al., Proc. Natl. Acad. Sci. 86:3833-3837, 1989). Alternatively, an "anchored polymerase chain reaction" may be performed (see Loh et al., Science 243:217-220, 1989). In this procedure, the first strand cDNA is primed with a 3' DNA primer as above, and a poly(dG tail) is then added to the 3' end of the strand with terminal deoxynucleotidyl transferase. The product is then amplified by PCR using the specific 3' DNA primer and another oligonucleotide consisting of a poly(dC) tail attached to a sequence with convenient restriction sites.

In some embodiments, at least the polynucleotides encoding the variable domains of the heavy and light chains are amplified. Strategies for performing single cell PCR to amplify sequences that encode antibodies for rabbits, mouse and humans, among others, are described in US20040067496, Kantor et al (Ann. NY Acad. Sci. 1995 764: 224-7), Boekel et al (Immunity. 1997 7:357-68), Yamagami et al (Immunity 1999 11:309-16), Beerli et al (MAbs. 2010 2), Morbach et al (Mol. Immunol. 2008 45:3840-6), Kiippers et al (Methods Mol Biol. 2004 271: 225-238) and Seidl et al (Int. Immunol. 1997 9:689-702), which are incorporated by reference herein. Several strategies for cloning antibody sequences by PCR are known and may be readily adapted for use in the instant method (e.g., by using a CDR-specific primer in addition to a disclosed primer). Such strategies include those described by: LeBoeuf (Gene. 1989 82:371-7), Dattamajumdar (Immunogenetics. 1996 43:141-51), Kettleborough Eur. J. Immunol. 1993 23:206-11), Babcook (Proc. Natl. Acad. Sci. 1996 93: 7843-7848) and Williams (Cold Spring Harb. Symp. Quant. Biol. 1989 54:637-47) as well as many others. In certain cases, the second primer may be a mixture of different primers or degenerate primers, for example.

Suitable restriction sites and other tails may be engineered into the amplification oligonucleotides to facilitate cloning and further processing of the amplification products. Amplification procedures using nested primers may also be used, where such nested primers are well known to one of skill in the art.

The obtained nucleic acid may be sequenced by any convenient method to obtain a) the sequence of a polynucleotide that encodes the variable domain of the heavy chain of an antibody and b) the sequence of a polynucleotide that encodes the variable domain of the light chain of an antibody, as well as the amino acid sequence of the encoded antibody.

Utility

In some embodiments, nucleic acid encoding an immunoglobulin heavy chain variable domain is isolated from an antibody producing cell. This nucleic acid may encode a heavy chain variable domain alone, or may encode a larger fragment of an immunoglobulin heavy chain, such as a heavy chain variable domain and part of the heavy chain constant region, or an entire immunoglobulin heavy chain, optionally including the N-terminal methionine and secretion signal of the immunoglobulin heavy chain. The nucleic acid encoding an immunoglobulin light chain variable domain is isolated from the same antibody-producing cell as the immunoglobulin heavy chain-encoding nucleic acid. This light chain-encoding nucleic acid may encode a light chain variable domain alone, or may encode a larger fragment of an immunoglobulin light chain, such as a light chain variable domain and part of the light chain constant region, or an entire immunoglobulin light chain, optionally including the N-terminal methionine and secretion signal of the immunoglobulin light chain.

The immunoglobulin encoding nucleic acids, once isolated from the cell, can be operably linked to an expression polynucleotide that will allow for expression, and optionally secretion of a functional antibody from a host cell. In particular cases, the expressed antibody may be a single chain antibody. Strategies for producing a recombinant antibodies, e.g., in mammalian, bacterial and yeast host cells are well known. Once an antibody molecule of the invention has been produced, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In many embodiments, antibodies are secreted from the cell into culture medium and harvested from the culture medium.

After a recombinant antibody is produced by another host cells, it may be tested in a variety of assays and, depending on how the antibody is going to be used, it may be humanized. For example, an antibody may be tested in a binding assay (e.g., an ELISA, a FACS assay or using immunohistochemistry) or an activity assay (which may be in vivo, in vitro or in a cell-free system), methods for which are well known (see, e.g., US20040067496).

An antibody produced by the instant methods finds use in, for example, diagnostics, in antibody imaging, and in treating diseases treatable by monoclonal antibody-based therapy. In particular, an antibody humanized by the instant methods may be used for passive immunization or the removal of unwanted cells or antigens, such as by complement mediated lysis or antibody mediated cytotoxicity (ADCC), all without substantial immune reactions (e.g., anaphylactic shock) associated with many prior antibodies.

In one embodiment, a humanized version of an identified antibody is provided. In certain cases, humanized antibodies may be made by substituting amino acids in the framework regions of a parent non-human antibody to produce a modified antibody that is less immunogenic in a human than the parent non-human antibody. Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332). In certain embodiments, framework substitutions are identified by modeling of the interactions of the CDR and framework residues to identify framework residues important for antigen binding and sequence comparison to identify unusual framework residues at particular positions (see, e.g., U.S. Pat. No. 5,585,089; Riechmann et al., Nature 332:323 (1988)). Additional methods for humanizing antibodies contemplated for use in the present invention are described in U.S. Pat. Nos. 5,750,078; 5,502,167; 5,705,154; 5,770,403; 5,698,417; 5,693,493; 5,558,864; 4,935,496; and 4,816,567, and PCT publications WO 98/45331 and WO 98/45332. In particular embodiments, a subject antibody may be humanized according to the methods set forth in published U.S. patent applications 20040086979 and 20050033031. Accordingly, the antibodies described above may be humanized using methods that are known in the art.

In one embodiment of particular interest, a subject antibody may be humanized in accordance with the methods set forth in great detail in U.S. Pat. No. 7,462,697 which application is incorporated by reference in its entirety. In general, this humanization method involves identifying a substitutable position of an antibody by comparing sequences of antibodies that bind to the same antigen, and replacing the amino acid at that position with a different amino acid that is present at the same position of a similar human antibody. In these methods, the amino acid sequence of a parental antibody is compared to (i.e., aligned with) the amino acid sequences of other antibodies that are clonally related to the parental antibody to identify variation tolerant positions. The amino acid sequence of the variable domain of the parental antibody may be compared to a database of human antibody sequences, and a human antibody that has an amino acid sequence that is similar to that of the parental antibody is selected. The amino acid sequences of the parental antibody and the human antibody are compared (e.g., aligned), and amino acids at one or more of the variation tolerant positions of the parental antibody are substituted by correspondingly positioned amino acids in the human antibody. In this humanization method, the CDR regions of the antibody may be humanized in addition to the framework regions.

The above-discussed variation tolerant position substitution methods are readily incorporated into any known humanization method and are also readily employed to produce humanized antibodies containing CDR regions that are altered with respect to the CDR regions of the parent antibody. Accordingly humanized antibodies containing altered versions of the CDRs of the above-described antibodies are provided.

As noted above, the subject antibody may be modified to provide a modified antibody. In particular embodiments, this method include making one or more amino acid substitutions (e.g., one, up to two, up to three, up to four or up to five of more, usually up to 10 or more). An amino acid substitution may be at any position, and the amino acid at that position may be substituted by an amino acid of any identity. In certain embodiments, a modified antibody may have the same general characteristics of the above-described rabbit antibodies. In one embodiment, after a substitutable position has been identified using the methods of U.S. Ser. No. 10/984,473, the amino acids at that position may be substituted. In particular embodiments, an amino acid substitution may be a humanizing substitution (i.e., a substitution that make the amino acid sequence more similar to that of a human antibody), a directed substitution (e.g., a substitution that make the amino acid sequence of an antibody more similar to that of a related antibody in the same group), a random substitution (e.g., a substitution with any of the 20 naturally-occurring amino acids) or a conservative substitution (e.g., a substitution with an amino acid having biochemical properties similar to that being substituted).

Antigens of interest include, but are not limited to, human surface-expressed or soluble proteins or carbohydrate molecules. Further preferred targets are surface-expressed proteins or carbohydrate molecules that are expressed on the surface of bacteria, viruses, and other pathogens, especially of humans. Antigens of interest include cytokines and chemokines, including but not limited to InterLeukin 1beta (IL1beta), IL2, IL4, IL5, IL7, IL8, IL12, IL13, IL15, IL18, IL21, IL23 and chemokines such as, for example, CXC chemokines, CC chemokines, C chemokines (or .gamma chemokines) such as XCL1 (lymphotactin-.alpha.) and XCL2 (lymphotactin-.beta.), and CX3C chemokines. Further included as preferred targets are receptor molecules of the cytokines and chemokines, including type I cytokine receptors such as, for example, the IL-2 receptor, type II cytokine receptors such as, for example, interferon receptors, immunoglobulin (Ig) superfamily receptors, tumor necrosis factor receptor family including receptors for CD40, CD27 and CD30, serine/threonine-protein kinase receptors such as TGF beta receptors, G-protein coupled receptors such as CXCR1-CXCR7, and tyrosine kinase receptors such as fibroblast growth factor receptor (FGFR) family members, EGF receptor family members including erbB1 (EGF-R; HER1), erbB2, (HER2), erbB3 (HER3), and erbB4 (HER4), insulin receptor family members including IGF-R1 and IGF-RII, PDGF receptor family members, Hepatocyte growth factor receptor family members including c-Met (HGF-R), Trk receptor family members, AXL receptor family members, LTK receptor family members, TIE receptor family members, ROR receptor family members, DDR receptor family members, KLG receptor family members, RYK receptor family members, MuSK receptor family members, and vascular endothelial growth factor receptor (VEGFR) family members.

Further preferred targets are targets that are over-expressed or selectively expressed in tumors such as, for example, VEGF, CD20, CD38, CD33, CEA, EpCAM, PSMA, CD54, Lewis Y, CD52, CD40, CD22; CD51/CD61, CD74, MUC-1, CD38, CD19, CD262 (TRAIL-R2), RANKL, CTLA4, and CD30; targets that are involved in chronic inflammation such as, for example, CD25, CD11a, TNF, CD4, CD80, CD23, CD3, CD14, IFNgamma, CD40L, LD50, CD122, TGFbeta and TGFalpha.

Other Embodiments

In certain cases the method described herein can employed using a reversible non-cross-linking fixative, thereby avoiding the need to uncrosslink the labeled cells prior to amplification. Such non-cross-linking fixatives include alcohols, including methanol and ethanol. As such, the method may in certain cases comprise: a) contacting a population of permeabilized, fixed, non-cross-linked antibody-producing cells with a labeled antigen to produce a labeled sample in which cells that produce an antibody that specifically binds to the antigen are intracellularly labeled; b) using fluorescence activated cell sorting (FACS) to isolate cells that are intracellularly labeled, thereby producing labeled cells; and d) amplifying heavy and light chain-encoding nucleic acid from individual labeled cells, thereby obtaining nucleic acid that encodes the variable domain of antibody that specifically binds to the antigen. Other steps of the method may stay the same.

EXAMPLES

The following examples are provided in order to demonstrate and further illustrate certain embodiments and aspects of the present invention and are not to be construed as limiting the scope thereof.

Example 1

Exemplary Protocol

A) Isolate peripheral blood mononuclear cells from a fresh blood sample using the density gradient centrifugation method
B) Resuspend isolated cells in RNAse free PBS
C) Fix cells with 1% paraformaldehyde in RNase free PBS on ice, for 20 minutes
D) Wash cells one time with RNase free cold PBS
E) Permeabilize and stain samples for 30 minutes on ice in cold RNase free 0.5% saponin/1% tryptone in PBS containing 10 μg/mL yeast tRNA and an appropriate dilution of a fluorescently labeled antibody/antigen
F) Wash cells one time with cold RNase free 0.1% saponin/1% tryptone in PBS containing 10 μg/mL yeast tRNA
G) Resuspend the cells in cold RNase free PBS containing 10 μg/mL yeast tRNA and store cells on ice
H) Sort cells with the desired labeling using FACS into 10 mM Tris solution containing RNase Inhibitor
I) Place sorted cells immediately on ice
J) Heat treat cells at 70° C. for 45 min to remove the chemical crosslinks
K) Lyse the cells on ice for 30 min in 10 mM Tris solution containing 0.5% TritonX-100 and RNase Inhibitor
L) Store cells at −20° C.
M) Thaw cells and perform a single cell RT-PCR reaction to amplify DNA corresponding to an antibody heavy chain and light chain N) Perform a nested PCR reaction using the single cell RT-PCR product to separately amplify the antibody heavy chain and light chain DNA

Example 2

A New Zealand white rabbit was immunized by subcutaneous injection of 0.2 mg alphafetoprotein (AFP), dissolved in 0.5 ml of PBS and emulsified with an equal volume of complete Freund adjuvant for priming immunization. The immunogen was divided up and injected into multiple sites along the back and legs. For booster immunization, a smaller total amount (0.1 mg) of immunogen emulsified with an equal volume of incomplete Freund adjuvant was used. Booster immunizations were given at 3-week intervals. Five days before blood collection and PBMC (peripheral blood mononuclear cell) isolation, the rabbit was given an IV boost of 0.2 mg AFP in 1 mL of PBS.

Figure 2:
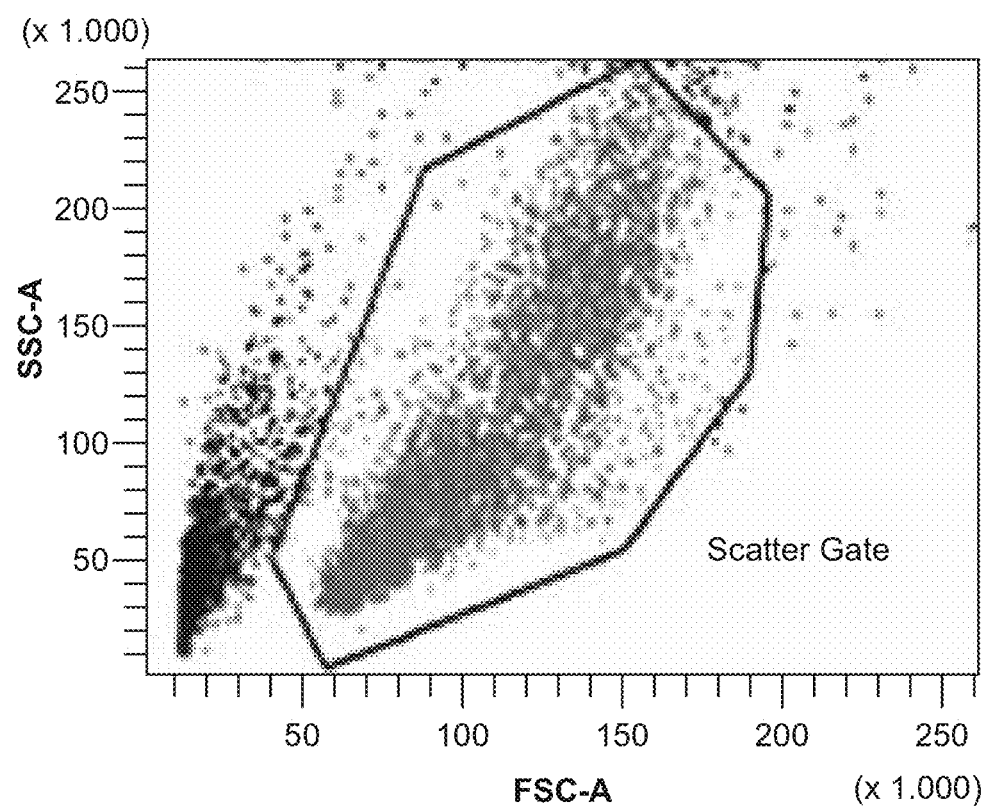
FIG. 2 is a scatter plot showing single stained cells that gated within the scatter.
Figure 3:
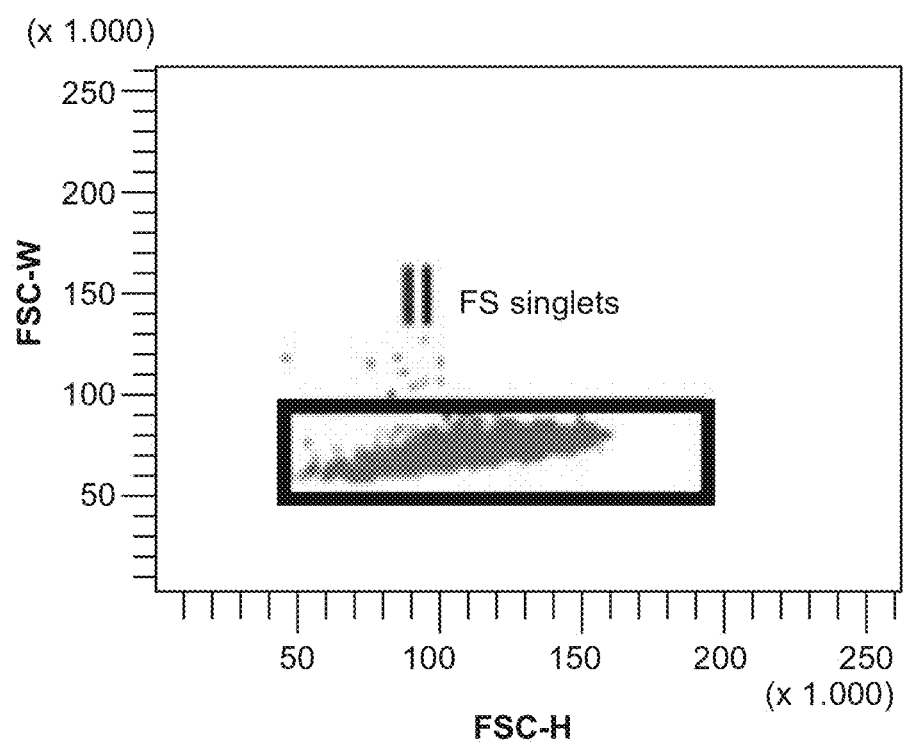
FIG. 3 is a scatter plot showing FS singlets.
Figure 4:
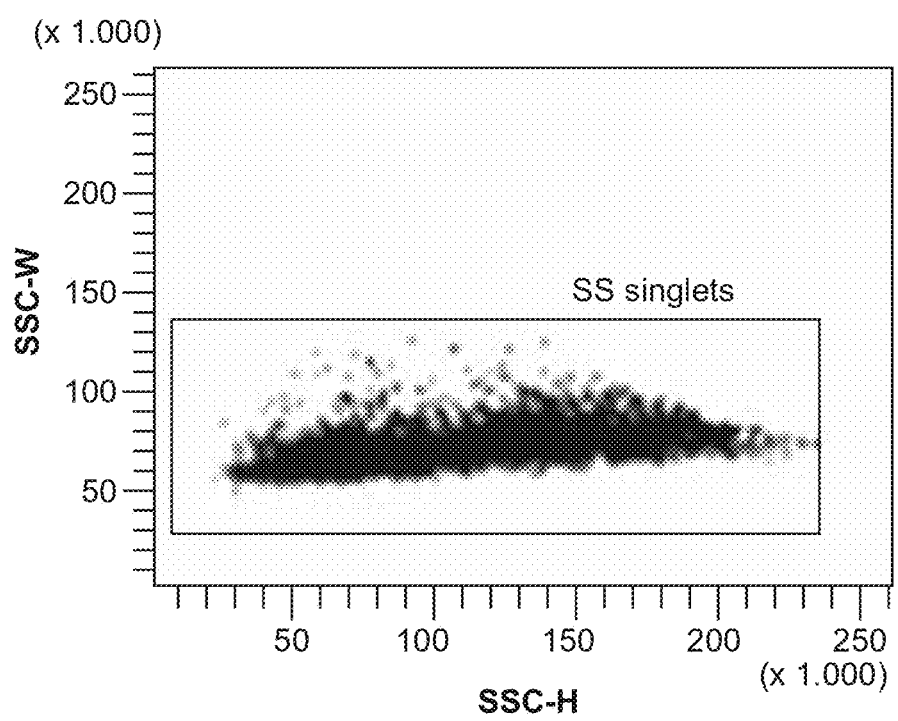
FIG. 4 is a scatter plot showing SS singlets.
Figure 5:
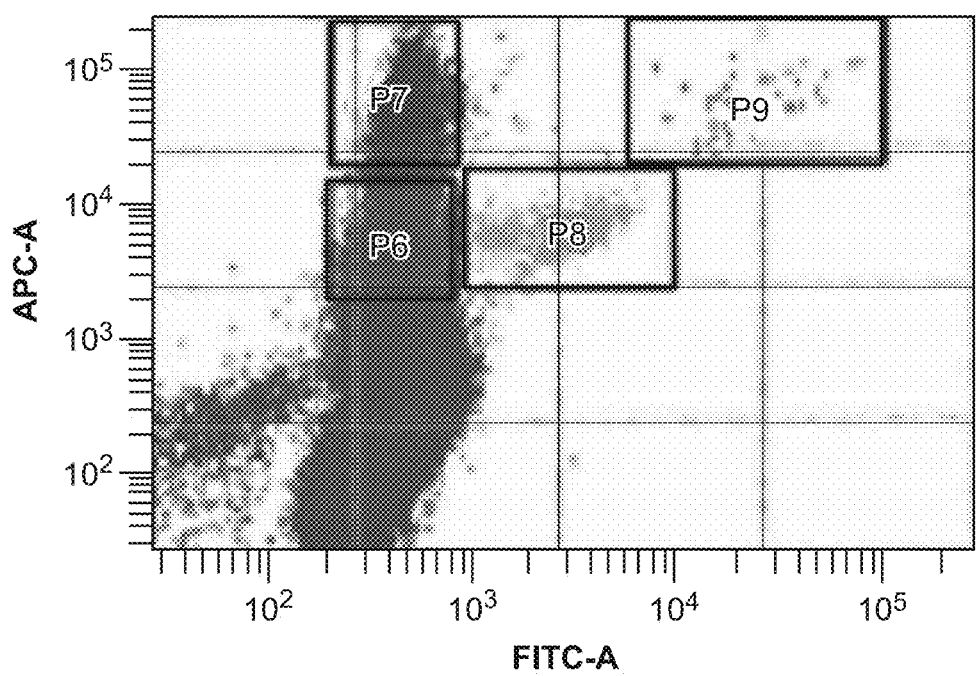
FIG. 5 is a scatter plot showing stained cells that gated within the P9 gates.

The isolated PBMCs were fixed with cold 4% paraformaldehyde in PBS, permeabilized with 1% tryptone/0.5% saponin in PBS, and then intracellularly stained with alphafetoprotein labeled with Alexa Fluor 488 (AFP AF488) and anti-rabbit IgG Fc specific—AF647. The stained cells were analyzed by FACS and single stained cells that gated within the scatter (FIG. 2), FS singlets (FIG. 3), SS singlets (FIG. 4), and P9 gates (FIG. 5) were sorted into a well of a 96-well plate containing lysis buffer.

After reverse crosslink by heat treatment, RT-PCR was performed for the single cells. Among 39 single cells tested, both light and heavy chains were obtained for 11 the cells (see FIGS. 8A-D and 9A-D).

Figure 6:
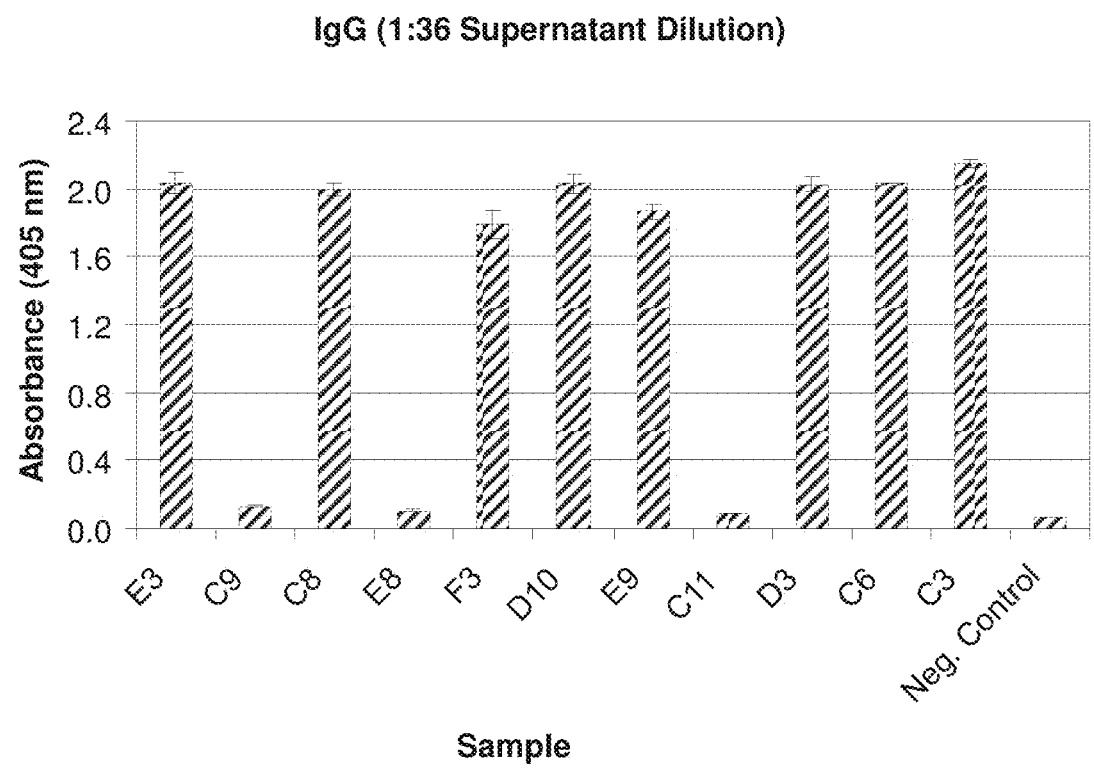
FIG. 6 is a graph showing results of an IgG ELISA.
Figure 7:
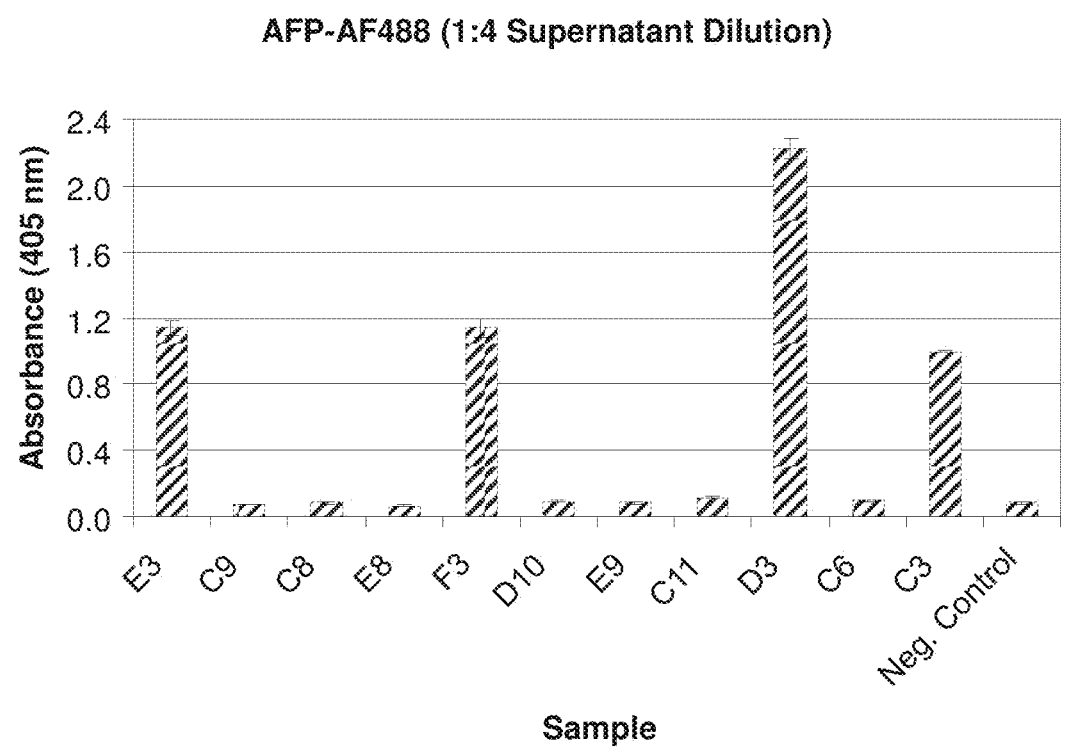
FIG. 7. Is a graph showing results of an antigen ELISA.

Recombinant antibodies were expressed in HEK 293 cells for the 11 light and heavy chains. The supernatants were tested by IgG and antigen ELISA. Eight of them expressed significant levels of IgG (FIG. 6) and four of them exhibited specificity for the alphafetoprotein antigen (FIG. 7).

What is claimed is:

1. A method comprising:
   a) contacting a population of permeabilized, reversibly cross-linked antibody-producing cells with a labeled antigen to produce a labeled sample in which cells that produce an antibody that specifically binds to said labeled antigen are intracellularly labeled;
   b) using fluorescence activated cell sorting (FACS) to isolate cells that are intracellularly labeled by the labeled antigen, thereby producing isolated labeled cells;
   c) uncrosslinking the isolated labeled cells to produce uncrosslinked cells; and
   d) amplifying heavy and light chain-encoding nucleic acid from the uncrosslinked cells, thereby obtaining nucleic acid that encodes the variable domain of antibodies that specifically bind to said labeled antigen.

2. The method of claim 1, wherein said permeabilized, reversibly cross-linked antibody-producing cells are from an animal that is mounting an immune response to said antigen.

3. The method of claim 2, wherein said antigen is an isolated peptide that is produced in vitro and administered to said animal.

4. The method of claim 2, wherein said animal has an immune response against an infection.

5. The method of claim 2, wherein said animal has an auto-immune disease.

6. The method of claim 2, wherein said animal is a rabbit, mouse or human.

7. The method of claim 1, wherein said population of permeabilized, reversibly cross-linked antibody-producing cells are permeabilized, reversibly cross-linked peripheral blood leukocytes.

8. The method of claim 1, wherein said permeabilized, cross-linked antibody-producing cells are permeabilized, reversibly cross-linked hybridomas.

9. The method of claim 1, wherein said amplifying is by single cell RT-PCR.

10. The method of claim 1, wherein said amplifying amplifies immunoglobulin gene sequences.

11. The method of claim 1, wherein said FACS deposits individual intracellularly labeled cells into individual vessels.

12. The method of claim 1, wherein said labeling comprises contacting said permeabilized, reversibly cross-linked antibody-producing cells with a fluorescently labeled peptide.

13. The method of claim 1, further comprising:
   labeling said permeabilized, reversibly cross-linked antibody-producing cells with a labeled secondary antibody that non-specifically binds to antibodies without interfering with binding of the labeled antigen; and
   using said fluorescence activated cell sorting (FACS) to isolate cells in said labeled sample that are labeled by both said labeled antigen and said secondary antibody.

14. The method of claim 1, wherein the permeabilized, cross-linked antibody-producing cells are crosslinked using formaldehyde.

15. The method of claim 1, further comprising sequencing said nucleic acid to obtain the nucleotide sequence of said variable domain of said antibody.

16. The method of claim 1, further comprising producing an antibody comprising said heavy chains recombinantly in another cell.

* * * * *